United States Patent [19]
Suzuki et al.

[11] Patent Number: 5,835,554
[45] Date of Patent: Nov. 10, 1998

[54] X-RAY IMAGING APPARATUS AND X-RAY GENERATION DETECTOR FOR ACTIVATING THE SAME

[75] Inventors: Masakazu Suzuki; Keisuke Mori, both of Kyoto; Akifumi Tachibana, Uji; Takao Makino, Otsu, all of Japan

[73] Assignee: J. Morita Manufacturing Corporation, Kyoto, Japan

[21] Appl. No.: 678,341

[22] Filed: Jul. 11, 1996

Related U.S. Application Data

[62] Division of Ser. No. 314,822, Sep. 29, 1994, Pat. No. 5,572,566.

[30] Foreign Application Priority Data

Nov. 30, 1993 [JP] Japan .................................. P5-300346
Nov. 30, 1993 [JP] Japan .................................. P5-300411
Nov. 30, 1993 [JP] Japan .................................. P5-300412
Nov. 30, 1993 [JP] Japan .................................. P5-300413

[51] Int. Cl.⁶ ...................................................... H05G 1/64
[52] U.S. Cl. ............................................ 378/98; 378/98.5
[58] Field of Search ...................................... 378/101, 108, 378/109, 110, 111, 112, 98.5, 98.27, 98

[56] References Cited

U.S. PATENT DOCUMENTS 4,928,295  5/1990  Tanaka ..................................... 378/112
4,991,192  2/1991  Nishiki .................................... 378/106
5,101,421  3/1992  Nishiki ..................................... 378/98

FOREIGN PATENT DOCUMENTS 7-506993  8/1995  Japan ............................... A61B 6/14

Primary Examiner—Don Wong
Attorney, Agent, or Firm—Koda and Androlia

[57] ABSTRACT

An image processor comprises a CPU, a ROM for storing programs and data, a main storage memory for storing image data, parameters for image processing and the like, an image memory for storing image data which are to be displayed on a monitoring device, a DA converter for outputting a signal to the external monitoring device or video printer, a DMA controller, a clock signal generator for driving an imager device such as a CCD sensor, an AD converter for converting an image signal SG from the imager device into a digital signal, an input/output circuit for generating a busy signal to an external X-ray controller and receiving an exposure signal from the X-ray controller, etc.

2 Claims, 15 Drawing Sheets

FIG. 2
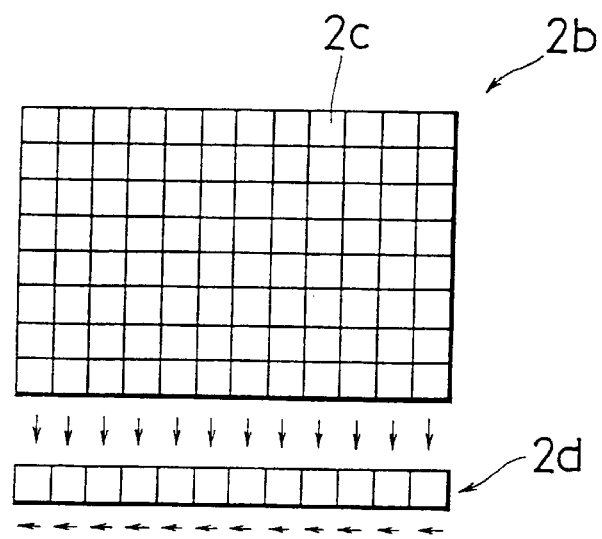
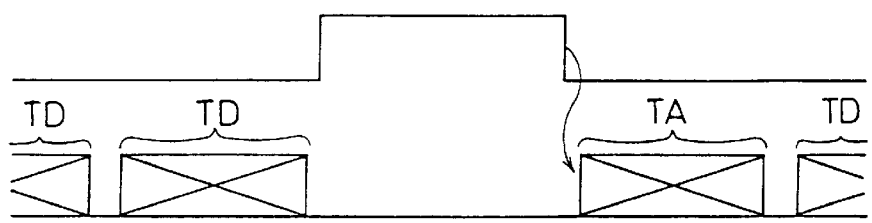
FIG. 3A EXP
FIG. 3B SG

F I G. 11A
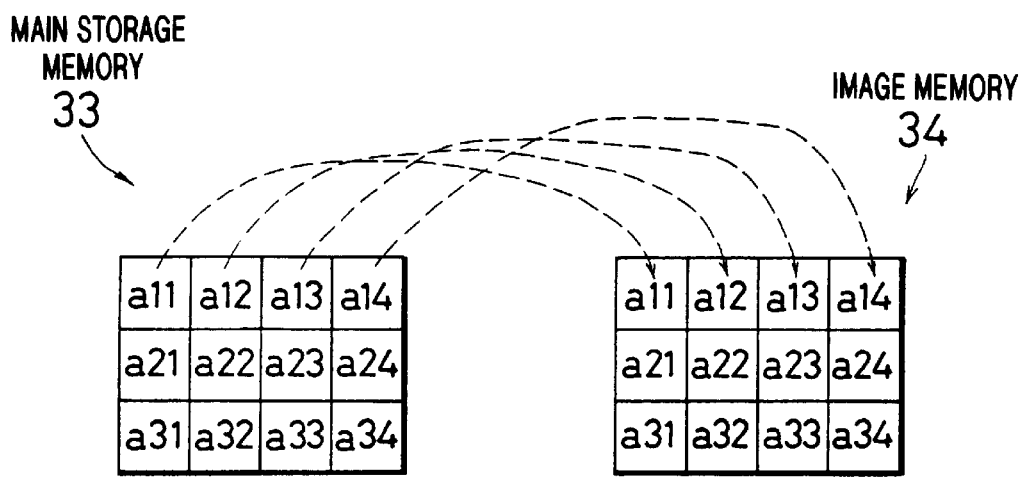
F I G. 11B
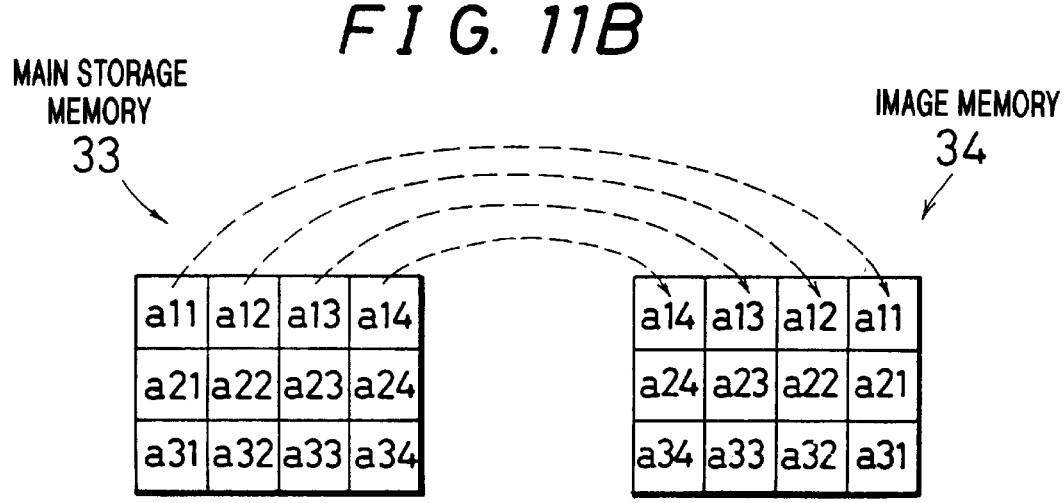

F I G. 17A
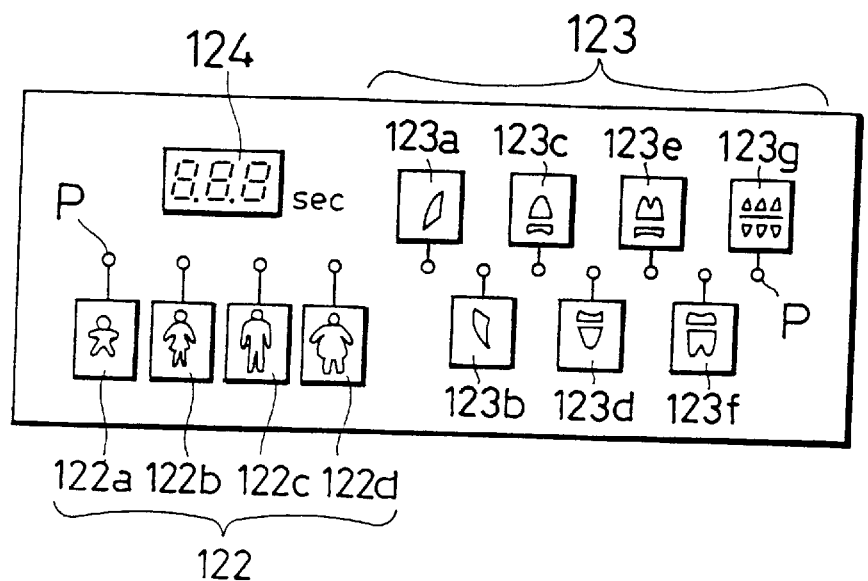
F I G. 17B
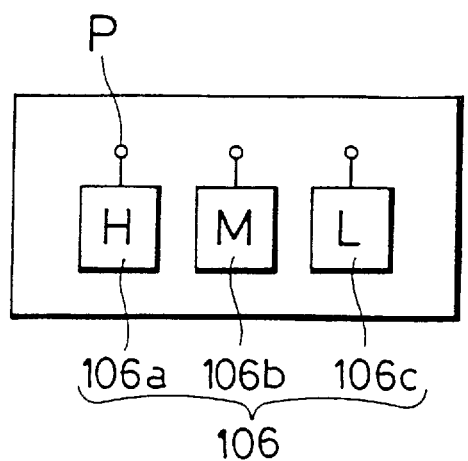

X-RAY IMAGING APPARATUS AND X-RAY GENERATION DETECTOR FOR ACTIVATING THE SAME

This is a division of application Ser. No. 08/314,822, filed Sep. 29, 1994, now U.S. Pat. No. 5,572,566.

BACKGROUND OF THE INVENTION

1. Field of the Invention

The present invention relates to an X-ray generation detector which detects the X-ray generation of an X-ray generator and outputs an X-ray exposure signal, and also to an X-ray imaging apparatus which detects in the form of an electric signal an X-ray image relating to an intraoral region or the like of a subject so that the X-ray image is displayed on a CRT (cathode ray tube) or the like.

2. Description of the Related Art

Conventionally, in order to obtain an X-ray image of an intraoral region, a film method is widely employed in which a photosensitive recording material such as a silver salt applied film is exposed to an X-ray image and the X-ray image is then subjected to developing and fixing processes.

However, the film method has problems including: 1) a time span of about 2 minutes or longer must be consumed between the X-ray radiography and the observation of the X-ray image; 2) a developing apparatus and processing solutions for conducting the developing and fixing processes are indispensable; 3) the X-ray sensitivity of a silver salt has a limitation and therefore an X-ray dose of a predetermined level is required to obtain a desired image density; and 4) it is impossible to correct an image which has been once fixed.

In order to solve these problems, an X-ray imaging apparatus is proposed in which an X-ray image is converted into an electric signal by using an imager device such as a CCD (charge coupled device) and the X-ray image is then displayed on a CRT (cathode ray tube) or the like. The X-ray imaging apparatus employs a so-called film-less method which does not use a photosensitive recording material such as a silver salt applied film, and has features including: 1) an X-ray image can be observed in real time after the X-ray radiography; 2) a developing apparatus and processing solutions are entirely unnecessary; 3) the X-ray sensitivity characteristic of an imager device is linear and therefore an X-ray dose can be reduced; and 4) a detected X-ray image can be subjected to various image processing, and easily copied or stored.

In the conventional film method, at the time when an X-ray film is positioned in the aral cavity of a patient, the preparation for X-ray exposure is completed so that the X-ray exposure can be done at any time thereafter.

On the other hand, in the X-ray imaging apparatus, a so-called idle reading operation in which charges (charges due to X-ray photon incidence, charges due to thermal excitation, etc.) accumulated in the light receiving portion of the imager device are periodically read out is conducted to reduce the dark current level of the imager device. Consequently, there arises a problem such that, when the X-ray radiography is conducted during this operation, a perfect X-ray image cannot be obtained. Furthermore, in a period when image processor conducts a predetermined image processing of an X-ray image obtained in the previous radiography, or another processing, even when another X-ray exposure is newly conducted on the imager device, the image processor cannot fetch a signal from the imager device, resulting in that the X-ray image formation ends in failure.

Moreover, the X-ray imaging apparatus is configured independently of an X-ray generator, and these two units do not connect with each other. This produces a problem such that the X-ray imaging apparatus cannot know the time when an X-ray radiography started and hence cannot decide the timing of starting the operation of reading an image from the imager device. Accordingly, the operator must separately control the X-ray generator and the X-ray imaging apparatus, thereby making the work of obtaining an X-ray image cumbersome. If the X-ray radiographing and the operation of reading an image from the imager device fail to establish a constant timing relationship between each other, furthermore, the dark current level and the noise level vary in each radiography, thereby producing a problem such that a stable X-ray image cannot be obtained.

In a usual dental Roentgen system, moreover, a film is set in the mouse of a patient, and an X-ray radiographing is then conducted by irradiating the face of the patient with X-rays so that an X-ray image of teeth or the like is recorded on the film in a positional relationship established in a direction along which the operator sees the patient. When the X-ray image recorded on the film is to be observed, such a positional relationship is convenient for the operator because the observation can be conducted as if the operator opposes the patient. Since an image of the right portion of the patient appears in the left portion of the film, however, the patient must observe the image in which the right and left sides are interchanged. Consequently, it is difficult for a patient inexperienced in the observation of an X-ray image to observe such an image.

In a conventional film photography, a mirror image can be obtained by turning over a film, and therefore the above-mentioned problem is not a serious one.

However, a conventional X-ray imaging apparatus wherein an X-ray image is displayed on a CRT or the like is not provided with a function of displaying a mirror image which is obtained by reversing an original image. When a dentist explains to a patient his(her) disease condition, therefore, it is unavoidable that the patient cannot fully understand his(her) disease condition, or the prolonged time for the explanation is required.

In a conventional X-ray imaging method using a silver salt applied film, the sensitivity of the film is fixed. By contrast, in an X-ray imaging apparatus using an imager device, however, the sensitivity is changed depending on the gain of a signal processing circuit. Specifically, when the X-ray dose (=X-ray intensity X irradiation time) is increased, the quantum efficiency of X-rays is decreased, so that a higher definite image is obtained, and when the X-ray dose is decreased, the image quality is lowered but the radiation exposure dose of a patient can be reduced. In this way, the X-ray radiation dose can be arbitrarily selected in consideration of the relationship between the balance of the image quality and the radiation exposure dose. In order to obtain an adequate image irrespective of the X-ray radiation dose, the X-ray radiation dose and the gain of the signal processing circuit must be linked together.

However, a conventional X-ray imaging apparatus is disposed independently of an X-ray generator. When X-ray generation conditions such as the X-ray radiation dose are to be adjusted, therefore, the X-ray generator must be operated, and when image process conditions such as the gain of a signal processing circuit are to be adjusted, the X-ray imaging apparatus must be operated. These make the adjusting operation very troublesome.

Furthermore, the X-ray radiation dose and the gain have a mutual relationship that an adequate image cannot be obtained unless one of the two values is increased and the other value is decreased. Consequently, it is not easy for the operator to control the two apparatuses while considering this relationship, or the operator is required to have long experience and skill.

SUMMARY OF THE INVENTION

It is an object of the invention to provide a dental X-ray imaging apparatus in which cooperation of X-ray exposure means and image processor is realized so that an erroneous X-ray exposure is prevented from occurring when the image processor means conducts a processing and hence cannot fetch an X-ray image from an imager device, thereby solving the above-discussed problems.

It is another object of the invention to provide an X-ray generation detector and an X-ray imaging apparatus in which cooperation of an X-ray generator and an image processing device is realized so that the workability of the X-ray imaging is improved, and the timing of an X-ray exposure and that of starting the operation of reading an image from an imager device are made constant so that a stable X-ray image is obtained.

It is a further object of the invention to provide an X-ray image display apparatus in which a mirror-reversed image of an X-ray image can be displayed so as to assist a patient in understanding the disease condition.

It is a still further object of the invention to provide an X-ray image display apparatus in which X-ray generation conditions and image processing conditions can be adjusted in a linked manner so that the operability of the X-ray imaging is improved and an X-ray image with an excellent quality can be obtained while preventing a patient from being exposed to X-rays in excess of that needed.

The dental X-ray imaging apparatus of the invention comprises:

an x-ray irradiator for irradiating X-rays to an intraoral region of a subject;

an imager device for detecting an X-ray image of the intraoral region; and an image processor for reading the X-ray image detected by the imager device and conducting a predetermined image processing, wherein a busy signal indicating that the image processor is conducting the processing is sent to the X-ray irradiator during a processing period of the image processor, and the X-ray irradiation is stopped when the X-ray irradiator receives the busy signal.

Furthermore, it is preferable in the invention that the X-ray irradiator comprises:

an X-ray generator; and an X-ray controller for generating a trigger signal for activating the X-ray generator, and the X-ray controller does not generate the trigger signal when the X-ray controller receives the busy signal.

Furthermore, it is preferable in the invention that the X-ray irradiator comprises:

an X-ray tube for generating X-rays; and a high voltage circuit for supplying a high voltage to the X-ray tube, and supplying a high voltage is stopped on the basis of the busy signal.

According to the invention, the busy signal indicating that the image processor is conducting the processing is sent to the X-ray irradiator during a processing period of the image processor, whereby the X-ray irradiator is enabled to recognize the processing state of the image processor. Furthermore, when the X-ray irradiator receives the busy signal, the X-ray irradiation is stopped. Even when the operator erroneously activates the X-ray irradiator, therefore, the X-ray irradiation to the subject is not conducted. Consequently, an erroneous X-ray irradiation to the subject can be prevented.

In the configuration wherein the X-ray irradiator comprises an X-ray generator, and an X-ray controller for generating a trigger signal for activating the X-ray generator, and the X-ray controller does not generate a trigger signal when the X-ray controller receives the busy signal, the generation of X-rays can be surely stopped.

In the configuration wherein the X-ray exposure means comprises an X-ray tube for generating X-rays, and a high voltage circuit for supplying a high voltage to the X-ray tube, and the supply of the high voltage is stopped on the basis of the busy signal, the generation of X-rays can be surely stopped.

In this way, even when the operator erroneously activates the X-ray irradiator during a processing period of the image processor, the X-ray irradiation to the subject is not conducted, whereby an erroneous X-ray irradiation can be surely prevented from occurring. Consequently, a useless X-ray irradiation to the subject can be suppressed and radiographing can be surely executed.

The X-ray generation detector of the invention is a detector which detects X-ray generation of an X-ray generator comprising an X-ray tube, and a high voltage circuit for applying a high voltage to the X-ray tube, and which comprises:

a voltage detector for detecting a voltage supplied to the high voltage circuit; and an exposure signal generator for generating an exposure signal indicating of an X-ray generation period on the basis of an output of the voltage detector.

The X-ray generation detector of the invention is a detector which detects X-ray generation of an X-ray generator comprising an X-ray tube, and a high voltage circuit for applying a high voltage to the X-ray tube, and which comprises:

a current detector for detecting a current supplied to the high voltage circuit; and an exposure signal generator for generating an exposure signal indicating an X-ray generation period on the basis of an output of the current detector means.

The X-ray generation detector of the invention is a detector which detects X-ray generation of an X-ray generator comprising an X-ray tube, and a high voltage circuit for applying a high voltage to the X-ray tube, and which comprises:

an x-ray detector for detecting X-rays radiated from the X-ray tube; and an exposure signal generator for generating an exposure signal indicating an X-ray generation period on the basis of an output of the X-ray detector.

The X-ray imaging apparatus of the invention comprises:

an X-ray generator for irradiating X-rays to a subject;

an imager device for detecting an X-ray image of the subject; and a image processor for reading the X-ray image detected by the imager device and conducting a predetermined image processing, wherein the apparatus further comprises any one of the above-mentioned X-ray generation detectors, and an operation of reading the X-ray image from the imager device is started on the basis of an exposure signal from the X-ray generation detector.

According to the invention, the voltage supplied to the high voltage circuit of the X-ray generator is detected by the voltage detector, whereby the actual period when a high voltage is applied to the X-ray tube is detected, and the exposure signal generator generates the exposure signal indicating an X-ray generation period on the basis of an output of the voltage detector, whereby an external device can be surely informed of the X-ray generation.

Furthermore, the current supplied to the high voltage circuit of the X-ray generator is detected by the current detector, whereby the actual period when a current flows through the X-ray tube is detected, and the exposure signal generator generates the exposure signal indicating an X-ray generation period on the basis of an output of the current detector, whereby an external device can be surely informed of the X-ray generation.

Furthermore, X-rays irradiated from the X-ray tube are detected by the X-ray detector, whereby the actual period when the X-ray tube generates X-rays is detected, and the exposure signal generator generates the exposure signal indicating an X-ray generation period on the basis of an output of the X-ray detector, whereby an external device can be surely informed of the X-ray generation.

Furthermore, according to the invention, any one of the above-mentioned X-ray generation detectors is provided, whereby the X-ray generation can be surely recognized, and the operation of reading the X-ray image from the imager device is started on the basis of an exposure signal from the X-ray generation detector, whereby linkage of the X-ray imaging operation and the image reading operation is realized, and the workability of the X-ray image formation is improved. Since the timing of an X-ray exposure and that of starting the operation of reading an image from the imager device are kept to be constant, the variations of the dark current level and noise level are reduced, so that an X-ray image with an excellent quality is obtained.

Furthermore, the X-ray image display apparatus of the invention comprises:

first and second storage means for storing X-ray image data of a subject;

data transferring means for transferring X-ray image data stored in the first storage means to the second storage means; and image displaying means for displaying X-ray image data stored in the second storage means, on a screen or a recording medium, wherein the data transferring means transfers the data to the second storage means in such a manner that the arrangement of the X-ray image data in the first storage means is mirror-reversed, and the apparatus further comprises transfer mode displaying means for displaying information indicating that the data transferring means conducts the data transfer while mirror-reversing the data.

Furthermore, it is preferable in the invention that the data transferring means comprises a transfer mode selecting means for selecting as a transfer mode one of the following modes: an normal mode in which data are transferred to the second storage means in accordance with the arrangement of the X-ray image data in the first storage means; and a reverse mode in which data are transferred to the second storage means while the arrangement of the X-ray image data in the first storage means is mirror-reversed.

According to the invention, the data transferring means such as a CPU (central processing unit), or a DMA (direct memory access) controller transfers data to the second storage means such as a RAM (random access memory) in such a manner that the arrangement of X-ray image data in the first storage means such as a RAM is mirror-reversed, whereby, when the X-ray image data stored in the second storage means are displayed on the screen or the recording medium, an image of the right portion of a patient appears in the right portion of a film. Accordingly an X-ray image which the patient can easily understand is obtained. Furthermore, since information indicating that the data transferring means conducts the data transfer while mirror-reversing the data is displayed on a screen, a recording medium or another display device, the attention of an observer such as the operator or the patient can be directed to the fact that the currently displayed X-ray image is a mirror-revered one. Consequently, the observer is prevented from misunderstanding the right and left relationship of the X-ray image.

Furthermore, the provision of the transfer mode selector for selecting as a transfer mode one of the following modes: an normal mode in which data are transferred to the second storage means in accordance with the arrangement of the X-ray image data in the first storage means; and a reverse mode in which data are transferred to the second storage means while the arrangement of the X-ray image data in the first storage means is mirror-reversed allows the mode to be easily switched from the normal display mode to the mirror-reverse mode and vice versa in accordance with the operation of the transfer mode selecting means. Therefore, the normal display of an X-ray image and the mirror-reversed display can be freely switched, so that the operator and the patient are assisted in understanding the displayed X-ray image.

Furthermore, the X-ray image apparatus of the invention comprises:

a X-ray generator for irradiating X-rays to a subject;

a X-ray controller for controlling an X-ray exposure period of the X-ray generator;

an imager device for imaging X-rays which have passed through the subject;

an amplifier for amplifying a signal from the imager device with a predetermined gain; and an image processor for processing a signal from the amplifying means and displaying the X-ray image, and is characterized in that the apparatus further comprises:

inputting means for inputting information of physical dimensions of the subject;

inputting means for inputting information of a radiographed region of the subject;

gain setting means for setting the gain of the amplifier; and decision means for determining the X-ray exposure period of the X-ray generator on the basis of the information of physical dimensions inputted through the physical dimension information inputting means, the information of the imaging region inputted through the imaging region information inputting means, and information of the gain set through the gain setting means.

Furthermore, the X-ray image apparatus of the invention comprises:

a X-ray generator for irradiating X-rays to a subject;

a X-ray controller for controlling an X-ray exposure period of the X-ray generating means;

an imager device for imaging X-rays which have passed through the subject;

an amplifier for amplifying a signal from the imager device with a predetermined gain; and an image processor for processing a signal from the amplifier and displaying the X-ray image, and is characterized in that the apparatus further comprises:

inputting means for inputting information of physical dimensions of the subject;

inputting means for inputting information of a radiographed region of the subject;

an image quality selector for selecting a quality of the X-ray image; and decision means for determining the X-ray exposure period of the X-ray generator and setting the gain of the amplifying means on the basis of the information of physical dimensions inputted through the physical dimension information inputting means, the imaging region information inputted through the imaging region information inputting means, and information of the image quality selected through the image quality selector.

According to the invention, since the transmissibility of X-rays changes depending on the physical dimensions of a subject, the imaging region and the like, the information of subject's physical dimensions and the imaging region are inputted through the physical dimension information inputting means and the imaging region information inputting means which are panel switches or the like. Since the signal level, quality etc. of an X-ray image change depending on the gain of the amplifier, the gain is set through the gain setting means such as a panel switch. On the basis of the physical dimension information, imaging region information, and gain information, the exposure period decision means such as a numeric operation circuit or a numeric table determines the X-ray exposure period. Therefore, the operator can easily and surely set adequate X-ray generation conditions and image processing conditions, only by indicating the physical dimension information, the imaging region information, and the gain information.

Furthermore, according to the invention, the physical dimension information of a subject, and the imaging region information are inputted through the physical dimension information inputting means, and the imaging region information inputting means which are panel switches or the like, and the image quality of an X-ray image, for example, a high definition image due to a high X-ray dose, or a rough image due to a low X-ray dose is selected. On the basis of these physical dimension information, imaging region information, and image quality information, the exposure period and gain decision means such as a numeric operation circuit or a numeric table determines the X-ray exposure period and the gain. Therefore, the operator can easily and surely set adequate X-ray generation conditions and image processing conditions, only by indicating the physical dimension information, the imaging region information, and the image quality information.

In this way, the operator can easily and surely set adequate X-ray generation conditions and image processing conditions by indicating the physical dimension information, the imaging region information, and the gain information or the image quality information. Moreover, it is possible to obtain an X-ray image which corresponds to the disease condition and is very adequate for diagnosis.

BRIEF DESCRIPTION OF THE DRAWINGS

Other and further objects, features, and advantages of the invention will be more explicit from the following detailed description taken with reference to the drawings wherein:

FIG. 2 is a diagram showing the configuration and operation of a CCD array sensor $2b$ of an imager device 2;

FIGS. 3A and 3B are timing charts showing the relationship between an X-ray irradiation and the reading operation of the imager device 2;

FIGS. 11A is a concept diagram showing the procedure of forwardly transferring data from a main storage memory 33 to a video memory 34;

FIG. 11B is a concept diagram showing the procedure of backwardly transferring data from a main storage memory 33 to a video memory 34;

FIG. 17A is a front view showing an example of a physical dimension selection switch 122 and an imaging region selection switch 123 of FIG. 16;

FIG. 17B is a front view showing an example of a gain selection switch 106 of FIG. 16;

DETAILED DESCRIPTION OF THE PREFERRED EMBODIMENTS

Figure 1:
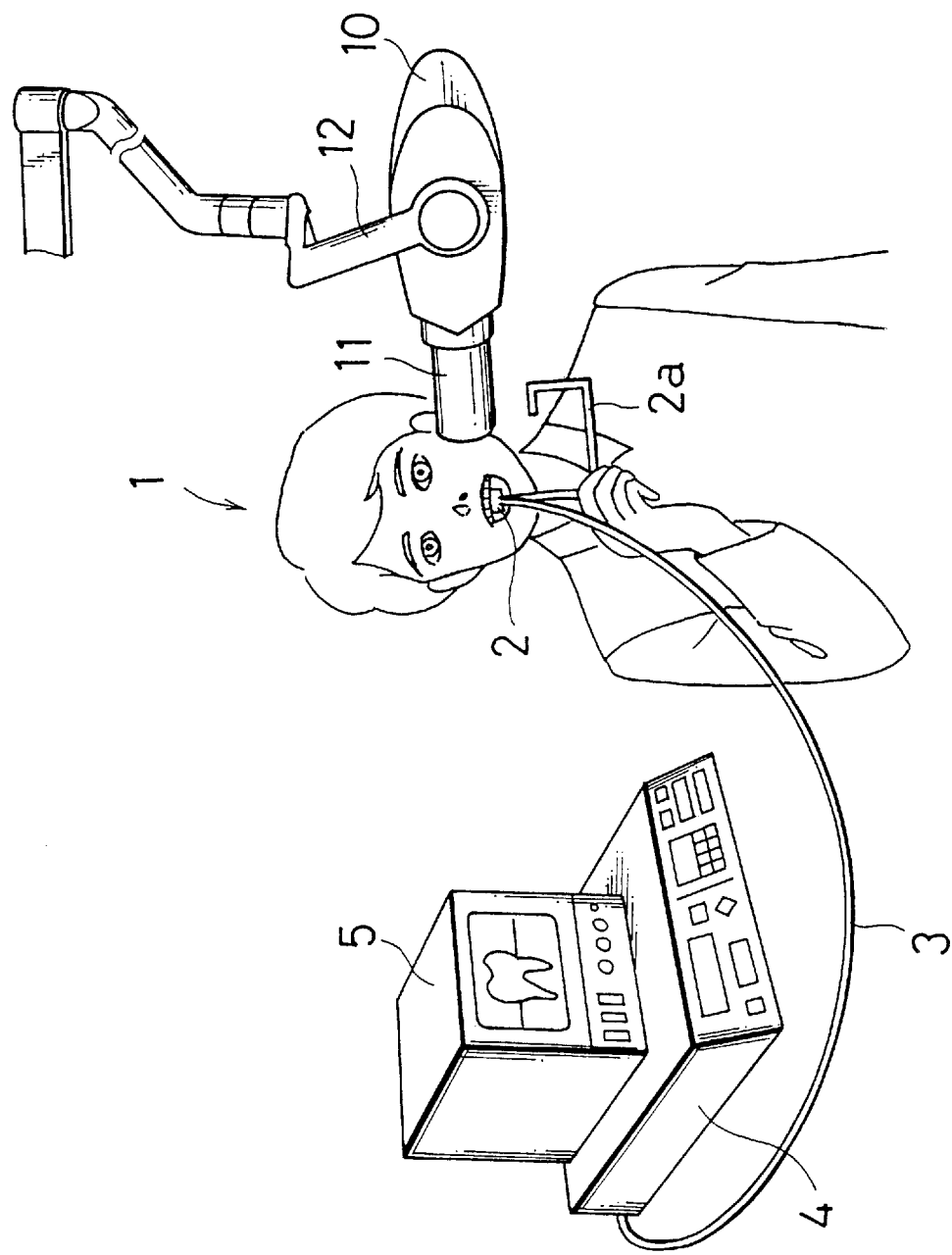
FIG. 1 is a diagram showing an engaged state of an X-ray imaging apparatus according to the invention.

Now referring to the drawings, preferred embodiments of the invention are described below.

FIG. 1 is a diagram showing an engaged state of an X-ray imaging apparatus according to the invention in the case where the subject is an intraoral region. An X-ray generator 10 is attached to a universal arm 12 in such manner that it is vertically swingable and horizontally rotatable in relation to the universal arm 12. The direction of an X-ray irradiation tube 11 can be adjusted so that X-rays are irradiated to the intraoral region of a patient 1.

On the other hand, an imager device 2 for detecting the distribution of X-rays, namely, X-ray image, passed through the intraoral region, is located at a position which is opposed to the X-ray irradiation tube 11 through the intraoral region between them. In FIG. 1, the patient holds with his(her) fingers a positioning member 2a fixed to the imager device 2, so that the imaging surface of the imager device 2 is directed in a X-ray irradiation direction.

The imager device 2 comprises a scintillator plate for converting X-ray photons into, for example, visible light, which is made of a compound containing rare earth elements, etc.; an optical fiber array which transmits the two-dimensional distribution of visible light radiated from the scintillator plate, as it is; and a CCD array sensor which receives the distribution of the visible light transmitted through the optical fiber array, accumulates generated charges, sequentially reads out the charges accumulated for a predetermined period and converts the charges into electrical signals. A lead plate for preventing scattered X-rays from entering is disposed on the back face of the CCD array sensor. These are disposed in a housing made of a synthetic resin or the like. An X-ray image detected by the imager device 2 is converted into an electric signal by the CCD array sensor, and then inputted into an image processor 4 through a signal cable 3.

The image processor 4 digitizes a signal from the imager device 2, stores the digital data in a memory, and then conducts a predetermined image processing on the digital data, whereby an image is displayed on a monitoring device 5 such as a CRT (cathode ray tube) or printed on a recording sheet to obtain a hard copy.

FIG. 2 is a diagram showing the configuration and operation of a CCD array sensor 2b of the imager device 2. The CCD array sensor 2b comprises a plurality of light receiving devices 2c which are arranged in a matrix of, for example, 600 pixels (lateral)×400 pixels (vertical), and a horizontal transfer shift register 2d which horizontally transfers charges generated in the light receiving devices 2c of the lowest row. The operation of the CCD array sensor will be described. 1) When light enters the sensor, charges corresponding to the light intensity distribution are generated in each light receiving devices and accumulated for a predetermined period. 2) Then, the vertical transfer by one light receiving device row is conducted, whereby the charges accumulated in each light receiving devices are transferred to the next light receiving device row, resulting in that the charges in the lowest light receiving device row are transferred to the horizontal transfer shift register 2d. 3) When a horizontal transfer is then conducted, charges stored in the horizontal transfer shift register 2d are read out in time series to be outputted as an analog signal. 4) The processes 1) through 3) are repeated until all charges accumulated in the light receiving devices 2c are read out. In this way, the light distribution received by the CCD array sensor 2b is detected as a time series image signal SG.

FIGS. 3A and 3B are timing charts showing the relationship between an X-ray irradiation and the reading operation of the imager device 2. When the X-ray irradiation is not conducted, charges accumulated in the imager device 2 are periodically read out in order to prevent excess charges due to thermal excitation and scattered X-rays from remaining in the device. Therefore, when an image signal SG of FIG. 3 (B) is outputted at an interval TD and an exposure signal EXP of FIG. 3 (A) indicating the timing of the X-ray exposure is changed to a high level, the reading operation of the imager device 2 is stopped and charges generated as a result of the X-ray exposure are accumulated. When the exposure signal EXP is changed to a low level, which means that the X-ray exposure has been ended, the reading operation of the imager device 2 is restarted to sequentially read out accumulated charges due to the X-ray exposure. Thereafter, the idle reading operation is again conducted.

Figure 4:
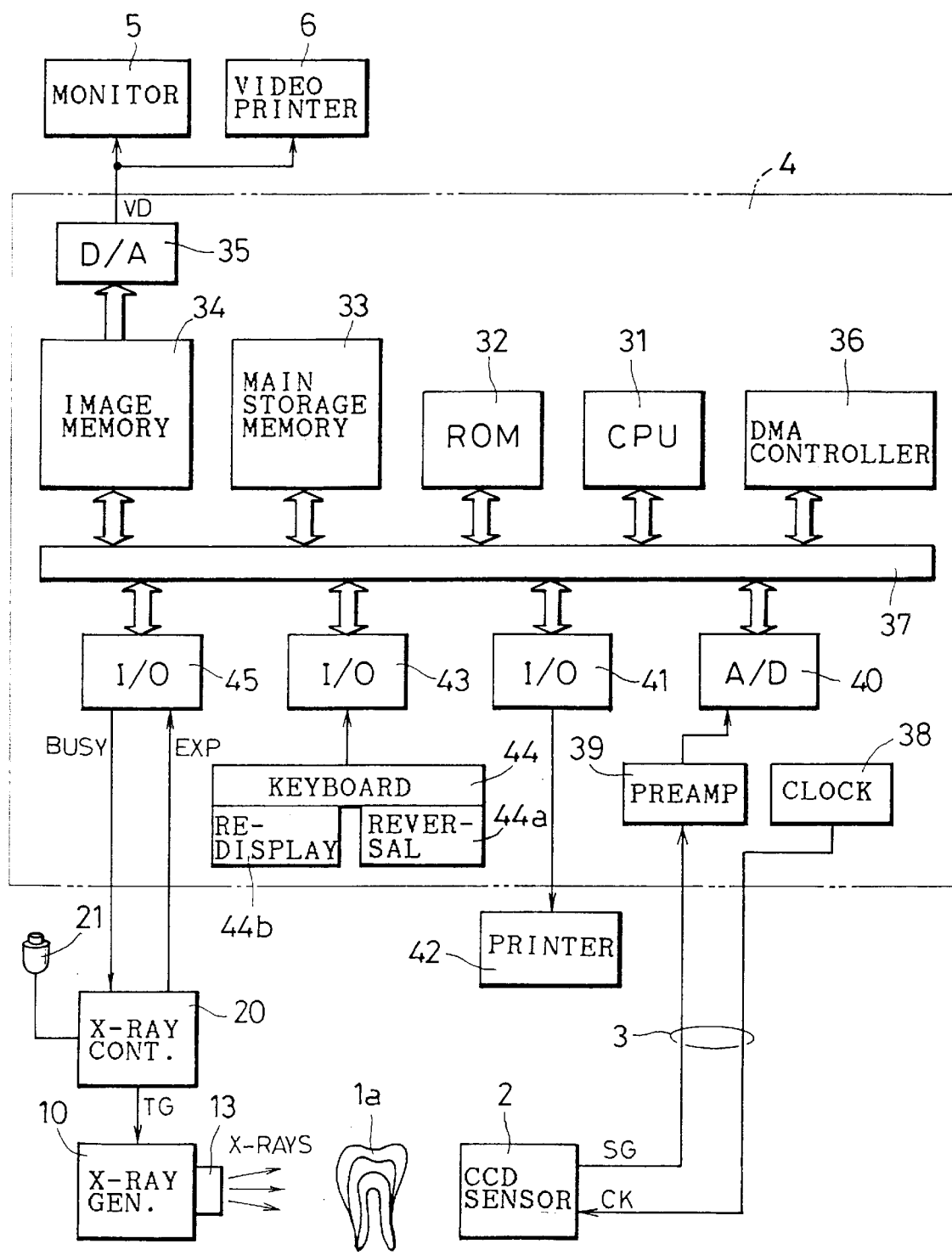
FIG. 4 is a block diagram showing an electrical configuration of an embodiment of the invention.

FIG. 4 is a block diagram showing an electrical configuration of an embodiment of the invention. The X-ray imaging apparatus comprises the X-ray generator 10 for irradiating X-rays to a subject 1a, an X-ray controller 20 for controlling the operation of the X-ray generator 10, the imager device 2 for detecting an X-ray image of the subject 1a, the image processor 4 for reading the X-ray image detected by the imager device, conducting a predetermined image processing and displaying the X-ray image, and a monitoring device 5 and a video printer 6 for displaying or recording image data processed by the image processor 4.

The image processor 4 comprises: a CPU (central processing unit) 31 for controlling the operations all over; a ROM (read only memory) 32 for storing programs and data required for the operation of the CPU 31; a main storage memory 33 for storing image data, and parameters required for calculations such as image processing; an image memory 34 for storing image data which are to be displayed on the monitoring device 5; a DA (digital to analog) converter 35 for converting image data stored in the image memory 34 into an analog video signal VD and outputting the signal to the monitoring device 5 or video printer 6; and a DMA (direct memory access) controller 36 for controlling data transfer between circuits without the engagement of the CPU 31; a clock signal generator 38 for generating a clock signal CK required for the operation of the imager device 2 such as a CCD sensor; a preamplifier 39 for receiving the image signal SG outputted from the imager device 2 and amplifying the signal; an AD (analog to digital)converting 40 for converting the analog signal outputted from the preamplifier 39 into a digital signal; an input/output circuit 41 for supplying data to an external printer 42; an input/output circuit 43 which comprises a reverse display switch 44a for instructing the mirror-reversing, and a redisplay switch 44b for instructing a redisplay, and which receives data from a keyboard 44 for data entry; an input/output circuit 45 for issuing a busy signal BUSY to the external X-ray controller 20 and receiving the exposure signal EXP from the X-ray controller 20; and a bus 37 for interconnecting these circuits.

In the imager device 2, charges accumulated for a predetermined period are periodically read out as a dark current on the basis of the clock signal CK from the clock signal generator 38, so that excess charges due to thermal excitation and scattered X-rays are prevented from remaining in the device.

The X-ray controller 20 outputs a trigger signal TG to the X-ray generator 10 in accordance with a direction from an exposure switch 21, and further outputs the exposure signal EXP indicating the generation of X-rays to the image processor 4. In response to the trigger signal TG, the X-ray generator 10 applies a high voltage to an X-ray tube 13 under predetermined X-ray exposure conditions including the tube voltage, the tube current, and the exposure period, and generates X-rays.

Next, the whole operation will be described. When the exposure switch 21 of the X-ray controller 20 is pressed, the X-ray generator 10 generates X-rays for a predetermined period. When the X-rays have reached the imager device 2 through the subject 1a, charges corresponding to the X-ray image irradiated on the imager device 2 are accumulated, and, after the X-ray exposure is ended, they are outputted in time series as the image signal SG. The image signal SG from the imager device 2 is supplied to the preamplifier 39 to be amplified to a given level, and then supplied to the AD converter 40 in the next stage to be converted into digital data. At this time, the DMA controller 36 occupies the bus 37, and image data output from the AD converter 40 are sequentially stored in a part of the main storage memory 33 through the bus 37.

On the other hand, even when the X-ray exposure is not conducted, the dark current of the imager device 2 is periodically read out, and then converted into digital data by the AD converter 40. The digital data are stored as dark current data in a part of the main storage memory 33.

The image data and dark current data stored in the main storage memory 33 are operationally processed by the CPU 31. For example, the dark current data are subtracted from the image data, and the resulting image data are again stored in a part of the main storage memory 33, whereby background noises can be erased from the image data so that image data of a high quality are obtained. In the case where dark current noises are negligible, the subtraction process may be omitted, so that the whole processing period is shortened.

The image data stored in the main storage memory 33 are transferred to the image memory 34 by the DMA controller 36. The stored contents of the image memory 34 are read out in time series to the DA converter 35 which in turn converts the digital image data into the analog video signal VD and outputs the signal to the monitoring device 5 or the video printer 6. In this way, the X-ray image detected by the imager device 2 is displayed on a screen of the monitoring device 5, or printed by the video printer 6 to obtain a hard copy. As required, the video signal VD may be recorded by a recording apparatus such as a video tape recorder.

Figure 5:
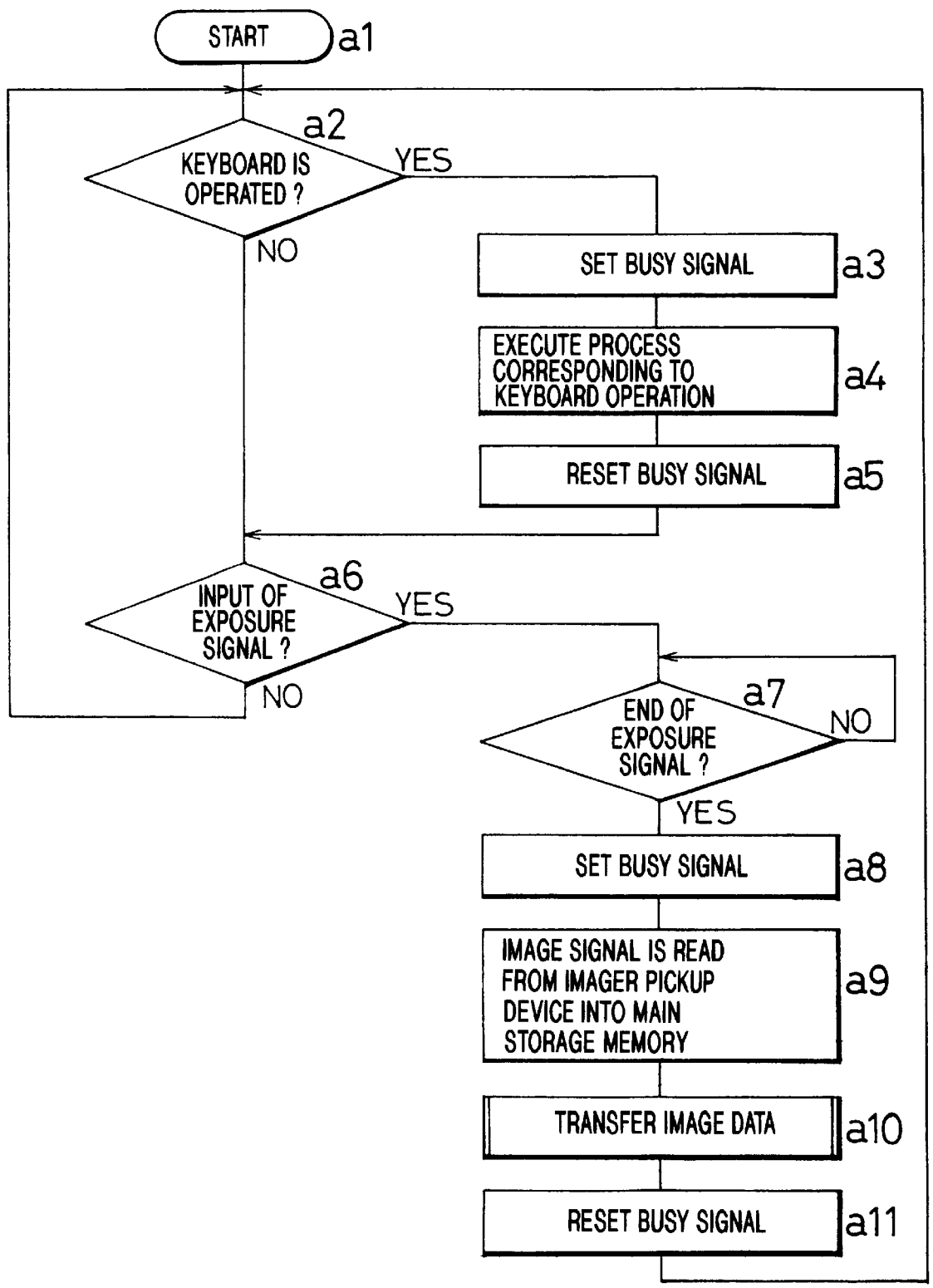
FIG. 5 is a flowchart showing the operation of the X-ray imaging apparatus shown in FIG. 4.

FIG. 5 is a flowchart showing the operation of the X-ray imaging apparatus shown in FIG. 4. First, the process starts from step a1, and the CPU 31 judges in step a2 whether the keyboard 44 has operated to input a command instructing a specific process or not. If the keyboard is not operated, the process proceeds to step a6. If the keyboard is operated, the process proceeds to step a3, and the CPU 31 sets the busy signal BUSY to be of a high level. The busy signal BUSY is coupled to the X-ray controller 20. When the busy signal BUSY is of a high level, the X-ray controller 20 judges that the image processor 4 is not ready for operating, and operates so as not to output a trigger signal TG to the X-ray generator 10. Under this state, even when the exposure switch 21 is pressed, the trigger signal TG is not output, and hence the X-ray generator 10 does not operate. Consequently, an erroneous X-ray exposure can be surely prevented from occurring during the processing of the image processor 4.

In next step a4, the CPU 31, or the DMA controller 36 executes the process corresponding to the command inputted through the keyboard operation. After this process is completed, in step a5 the CPU 31 resets the busy signal BUSY to be of a low level, and the process then proceeds to step a6. When the busy signal BUSY is of a low level, the X-ray controller 20 judges that the image processor 4 is ready for operating, and allows the trigger signal TG to be issued. Under this state, when the exposure switch 21 is pressed, the trigger signal TG is outputted and X-rays are generated from the X-ray tube 13 of the X-ray generator 10 under predetermined X-ray exposure conditions.

In step a6, the CPU 31 judges whether the exposure signal EXP from the X-ray controller 20 is supplied to the image processor 4 or not. The exposure signal EXF informs the image processor 4 of the times of starting and ending the X-ray exposure. For example, the exposure signal EXP is kept to be of a high level for the period from the start to the end of the exposure, and it is kept to be of a low level in the remaining period. If the exposure signal EXP is not inputted in step a6, the process returns to step a2. In contrast, if the exposure signal EXP of, for example, a high level is inputted, that means that the X-ray generator 10 is irradiating with X-rays. Therefore, the reading operation of the imager device 2 is stopped and charges are accumulated. Then, the process proceeds to next step a7, and waits until the X-ray exposure is ended and the level of the exposure signal EXP is changed to, for example, a low level.

When the level of the exposure signal EXP is changed, for example, to a low level, the process proceeds to next step a8. In the same manner as step a3 described above, the CPU 31 sets the busy signal BUSY to be of a high level, and the image processor 4 operates so as not to output the trigger signal TG, and inhibits the X-ray exposure.

In next step a9, the reading operation of the imager device 2 is started, and then the image signal SG of the subject 1a which is outputted from the imager device 2 is supplied to the main storage memory 33 through the preamplifier 39, the AD converter 40, and the bus 37. Thereafter, if necessary, the processing of subtracting the dark current data, and image processing such as negative-positive reversal, magnification, upside down inversion, density conversion, and coloring are executed by the CPU 31 to prepare image data for display. An image data transfer routine (described below in detail) in which data are transferred from the main storage memory 33 to the video memory 34 and an image is displayed is executed in next step a10.

After the process of the image processor 4 is ended, in next step all the CPU 31 resets the busy signal BUSY to be a of low level. Thereafter the process returns to step a2 to judge in succession whether the keyboard is operated or not and whether the exposure signal EXP is inputted or not.

As described above, when the image processor 4 executes any processing, the fact that it is in the midst of processing is notified to the X-ray controller 20. This allows the X-ray controller 20 to judge whether the X-ray exposure can be done or not. Therefore, it is possible to prevent the X-ray exposure from being started before the image processor 4 is ready for operating.

Additionally, the operation of reading an X-ray image from the imager device 2 is started on the basis of the exposure signal EXP, whereby the X-ray imaging operation and the image reading operation are associated with each other. Consequently, the workability of the X-ray imaging is improved. Further, since the timing of an X-ray exposure and that of starting the operation of reading an image from the imager device are kept to be constant, an X-ray image with an excellent quality can be obtained.

In the above, an embodiment in which the exposure signal EXP is generated in a software operation of the X-ray controller 20 has been described. Alternatively, an exposure signal EXP obtained from an X-ray generation detector which will be described below may be used.

Figure 6:
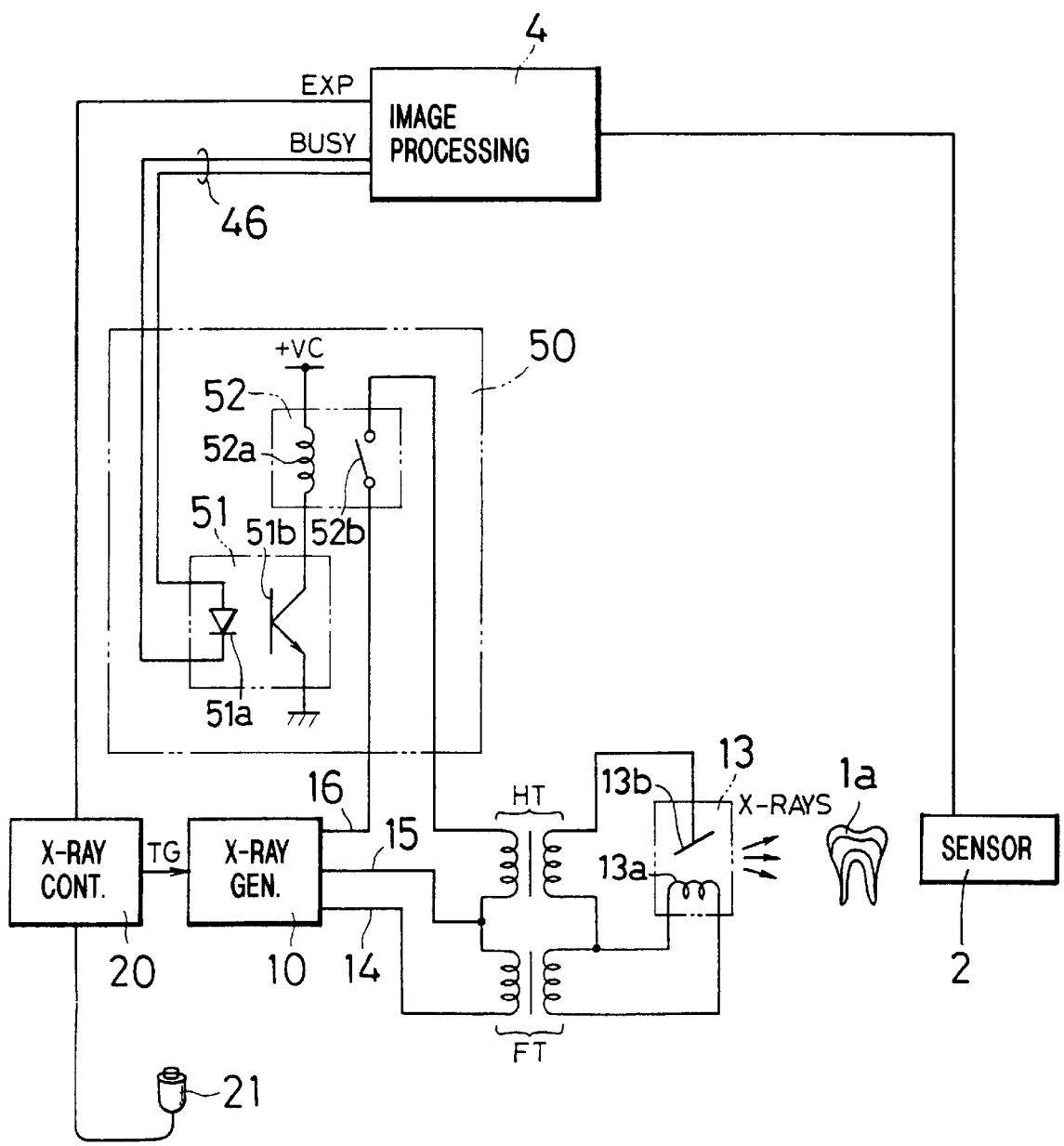
FIG. 6 is a block diagram showing an electrical configuration of another embodiment of the invention.

FIG. 6 is a block diagram showing an electrical configuration of another embodiment of the invention. The embodiment is configured in the similar manner as that of FIG. 4 except that the busy signal BUSY outputted from the image processor 4 is supplied to an X-ray generation allowing device 50, and the high voltage circuit of the X-ray generator 10 is directly closed/opened by the X-ray generation allowing device 50 in accordance with the level of the busy signal BUSY.

The X-ray generation allowing device 50 comprises a photocoupler 51 to which a current loop 46 for transmitting the busy signal BUSY is to be connected, and a relay 52 for closing/opening the high voltage circuit of the X-ray generator 10.

The X-ray generator 10 supplies electric power through a filament line 14, a common line 15, and a high voltage line 16. The primary winding of a filament transformer FT is connected between the filament line 14 and the common line 15, and the primary winding of a high voltage transformer HT is connected between the common line 15 and the high voltage line 16. A switch 52b of the relay 52 is disposed in the middle of the high voltage line 16. The secondary winding of the filament transformer FT is connected to the filament 13a of the X-ray tube 13, and the secondary winding of the high voltage transformer HT is disposed between the anode target 13b and the filament 13a of the X-ray tube 13. Although the high voltage circuit shown in FIG. 6 is an example of a preheating system in which two transformers, namely the high voltage transformer HT and the filament transformer FT, are used and each transformer is started with a certain time lag, according to the invention, a simultaneous heating system in which a single transformer executes both functions may be also employed.

Next, the whole operation will be described. When the image processor 4 executes any processing or is under the so-called busy state, substantially no current flows through the current loop 46 and a light emitting diode 51a of the photocoupler 51 does not emit light, whereby a phototransistor 51b is put into a cut off condition. The phototransistor 51b is connected to the relay 52 so as to drive the coil 52a. When the phototransistor 51b is turned off, the relay 52 does not operate and the switch 52b is opened, whereby the high voltage line 16 of the X-ray generator 10 is disconnected. Under this state, even when the exposure switch 21 is pressed down, the X-ray controller 20 outputs the trigger signal TG, and the X-ray generator 10 starts to operate, no voltage is applied to the X-ray tube 13 because of the disconnection of the high voltage line 16 and hence X-rays are not generated.

In contrast, when the image processor 4 executes no process or is under the so-called not-busy state, a current of a predetermined level flows through the current loop 46 and the light emitting diode 51a emits light, whereby the phototransistor 51b is put into a conductive condition. When the phototransistor 51b is turned on, the relay 52 is activated to close the switch 52b, whereby the high voltage line 16 of the X-ray generator 10 is connected. Under this state, when the exposure switch 21 is pressed down, the X-ray controller 20 outputs the trigger signal TG and the X-ray generator 10 starts to operate.

Hereinafter, the operation will be described further with taking the preheating system as an example. First, a filament current of a predetermined level flows through the filament line 14 and the filament 13a of the X-ray tube 13 is heated. Then, a voltage of a predetermined level is applied to the high voltage line 16, whereby a tube voltage of a predetermined level is applied to the anode target 13b of the X-ray tube 13. As a result, a tube current of a predetermined level flows for a predetermined exposure period, and X-rays are generated from the anode target 13b.

In this way, when the image processor 4 executes any processing, the supply of the high voltage to the X-ray tube 13 is compulsorily stopped on the basis of the busy signal BUSY indicating that the image processor 4 is conducting a processing, whereby the X-ray imaging can be prevented from being started before the image processor 4 is ready for operating. The embodiment has an advantage that the above-described configuration can be realized only by slightly modifying the manner of connection in a high voltage circuit of an existing X-ray apparatus. Consequently, linkage of an X-ray generator and an X-ray imaging apparatus using a CCD sensor can easily be realized.

Figure 7A:
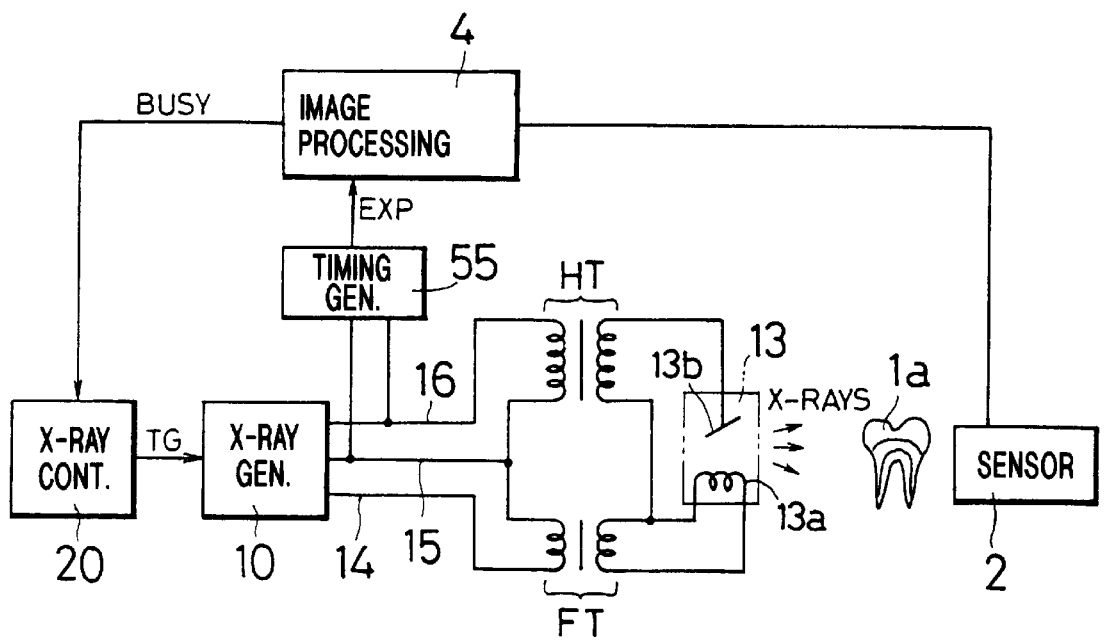
FIG. 7A is a block diagram showing an example of an X-ray generation detector which is applied to an X-ray imaging apparatus according to the invention.
Figure 7B:
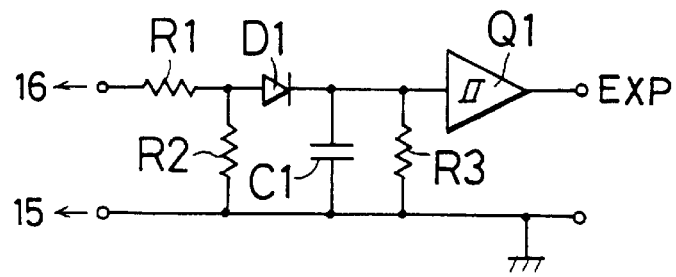
FIGS. 7B and 7C show specific examples of a timing generator 55 shown in FIG. 7A.
Figure 7C:
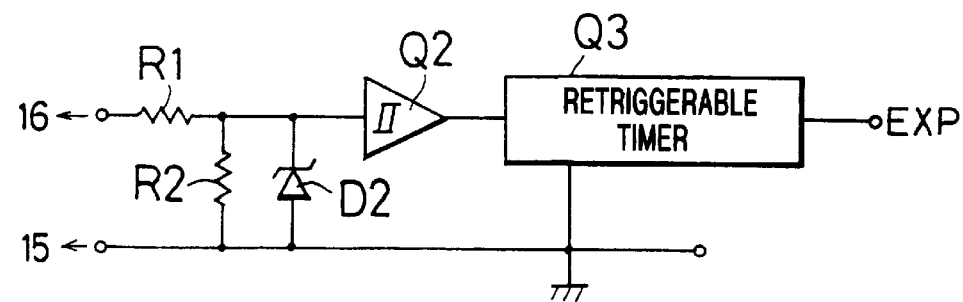

FIG. 7A is a block diagram showing an example of an X-ray generation detector which is applied to an X-ray imaging apparatus according to the invention, and FIGS. 7B and 7C show specific examples of a timing generator 55 shown in FIG. 7A.

First, the high voltage circuit of the X-ray generator 10 will be described. The X-ray generator 10 supplies the power to the X-ray tube through the filament line 14, the common line 15, and the high voltage line 16. The primary winding of the filament transformer FT is connected between the filament line 14 and the common line 15, and the primary winding of the high voltage transformer HT is connected between the common line 15 and the high voltage line 16. The secondary winding of the filament transformer FT is connected to the filament 13a of the X-ray tube 13, and the secondary winding of the high voltage transformer HT is connected between the anode target 13b and the filament 13a of the X-ray tube 13.

The operation will be described. First, a filament current of a predetermined level flows through the filament line 14 and the filament 13a of the X-ray tube 13 is heated. Then, a voltage of a predetermined level, such as a commercial power of a frequency of 60 Hz is applied to the high voltage line 16, whereby a tube voltage of a predetermined level is applied to the anode target 13b of the X-ray tube 13. For a period within a predetermined exposure period in which the potential of the anode target 13b is made positive by the self-rectifying function of the X-ray tube 13, a tube current of a predetermined level flows, and X-rays are generated from the anode target 13b. Although the high voltage circuit shown in FIG. 7A is an example of the preheating system in which two transformers, namely the high voltage transformer HT and the filament transformer FT are used, according to the invention may be also employed the simultaneous heating system in which a single transformer executes both functions of the two transformers.

The timing generator 55 which constitutes the X-ray generation detector is connected to the common line 15 and the high voltage line 16 of the X-ray generator 10. First, the circuit example of FIG. 7B will be described. The timing generator 55 comprises resistors R1 and R2 which divide the voltage supplied to the high voltage line 16 of the X-ray generator 10 in order to detect it as a low voltage signal; a diode D1, a capacitor C1 and a resistor R3 by which the detected voltage signal are rectified and smoothed; and a Schmitt trigger Q1 which shapes the waveform of the rectified and smoothed signal to generate an exposure signal EXP. A commercial power (e.g., 60 Hz) is supplied to the high voltage line 16 of the X-ray generator 10. The division ratio of the resistors R1 and R2 is selected so that the voltage conforms to the TTL (transistor transistor logic) level.

The operation of the timing generator will be described. The AC voltage applied to the high voltage line 16 is divided by the resistors R1 and R2 and then subjected to half-wave rectification by the diode D1, whereby the upper half portion of the sinusoidal wave is taken out in each cycle of the power source frequency in a predetermined exposure period. The rectified voltage is smoothed by the capacitor C1 to produce a pulsating signal corresponding to the predetermined exposure period. The pulsating signal is binarized with a predetermined threshold level by the Schmitt trigger Q1, and the exposure signal EXP is outputted as a digital signal corresponding to the predetermined exposure period, and supplied to the image processor 4 shown in FIG. 4.

Next, the circuit example of FIG. 7C will be described. The timing generator 55 comprises the resistors R1 and R2 which divide the voltage supplied to the high voltage line 16 of the X-ray generator 10 in order to detect it as a low voltage signal; a zener diode D2 which rectifies the detected voltage signal and clips at a predetermined level; a Schmitt trigger Q2 which shapes the waveform of the rectified signal; and a retriggerable timer Q3 which can be retriggered by a pulse that is reinputted within a given period.

The operation of the timing generator will be described. The AC voltage applied to the high voltage line 16 is divided by the resistors R1 and R2 and then subjected to half-wave rectification by the zener diode D2, whereby the upper half portion of the sinusoidal wave is taken out in each cycle of the power source frequency in a predetermined exposure period. The level of the rectified voltage is limited by the clip level, whereby the voltage has a pulse-like shape. The pulse-like voltage is subjected to pulse shaping with the Schmitt trigger Q2 and converted into a digital signal in the form of continuous pulse signals with the retriggerable timer Q3. The digital signal is outputted as the exposure signal EXP corresponding to the predetermined exposure period. The exposure signal EXP is supplied to the image processor 4 shown in FIG. 4.

In this way, the period when a high voltage is applied to the X-ray tube can be detected by detecting the voltage applied to the high voltage line 16 of the X-ray generator 10. Therefore, the X-ray generation can be surely known. The X-ray generation detector shown in FIG. 7 has an advantage that the above-described configuration can be realized only by slightly modifying the manner of connection in a high voltage circuit of an existing X-ray apparatus. Consequently, linkage of an X-ray generator and an X-ray imaging apparatus using a CCD sensor can be easily realized.

Figure 8:
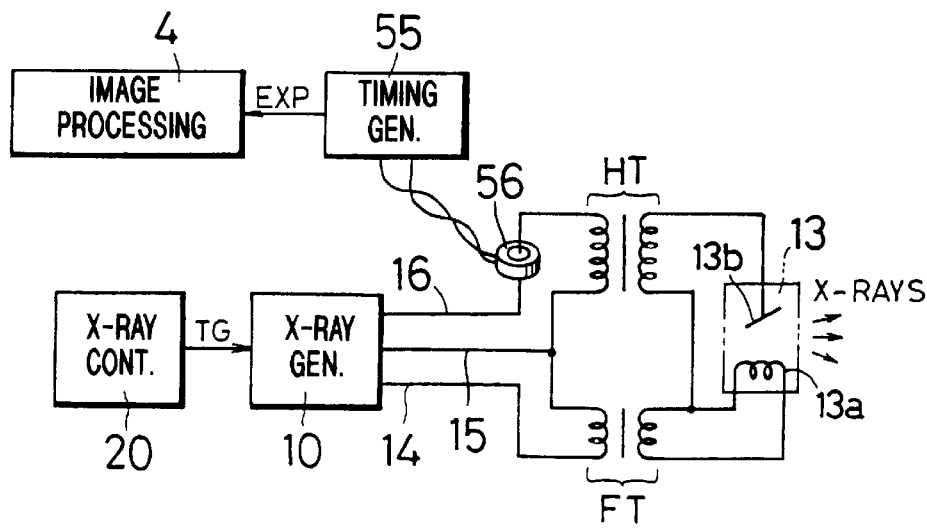
FIG. 8 is a block diagram showing another example of an X-ray generation detector which is applied to an X-ray imaging apparatus according to the invention.

FIG. 8 is a block diagram showing another example of an example of an X-ray generation detector which is applied to an X-ray imaging apparatus according to the invention. The X-ray generation detector comprises a current detecting device 56 for detecting a current flowing through the high voltage line 16, and the timing generator 55 which generates an exposure signal EXP on the basis of a signal outputted from the current detecting device 56. The current detecting device 56 detects magnetic fields produced by a current flowing through the high voltage line 16. The type of the current detecting device includes a transformer type in which a magnetic field intensity is converted into a voltage signal on the principle of electromagnetic induction and a Hall element type in which a magnetic field intensity is converted into a voltage signal by the Hall effect. The timing generator 55 may be configured by the circuit of FIG. 7B consisting of the voltage conversion unit, the rectifying and smoothing unit, and the waveform shaping circuit, the circuit of FIG. 7C consisting of the voltage conversion unit, the rectifying unit, the waveform shaping circuit, and the signal shaping unit, or the like. The exposure signal EXP outputted from the timing generator 55 is supplied to the image processor 4 shown in FIG. 4.

In this way, the period when a current flows through the X-ray tube can be detected by detecting the current supplied to the high voltage line 16 of the X-ray generator 10. Therefore, the X-ray generation can be surely known. The X-ray generation detector shown in FIG. 8 has an advantage that the above-described configuration can be realized only by attaching the current detecting device 56 to the high voltage line 16 without changing the manner of connection in a high voltage circuit of an existing X-ray apparatus. Consequently, linkage of an X-ray generator and an X-ray imaging apparatus using a CCD sensor can be easily realized.

Figure 9A:
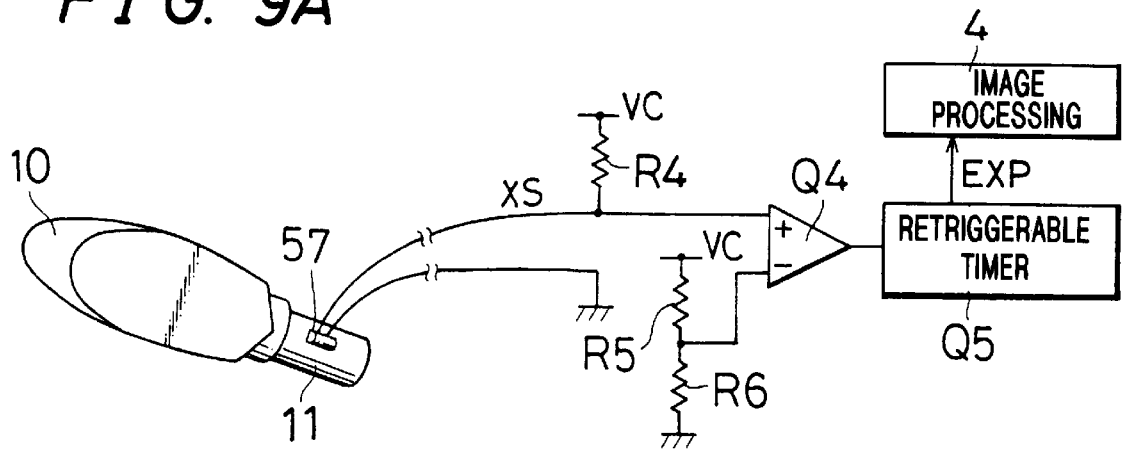
FIG. 9A is a block diagram showing a further example of an X-ray generation detector which is applied to an X-ray imaging apparatus according to the invention.

FIG. 9A is a block diagram showing a further example of an X-ray generation detector which is applied to an X-ray imaging apparatus according to the invention. The X-ray generation detector comprises an X-ray detecting device 57 which is fixed to an inner circumferential surface of the X-ray irradiation tube 11 of the X-ray generator 10; a comparator Q4 which compares a detection signal XS from the X-ray detecting device 57 with a predetermined threshold level to binarize the signal; and a retriggerable timer Q5 which shapes a pulse signal outputted from the comparator Q4. The X-ray detecting device 57 is of the type in which X-rays radiated from the X-ray generator 10 are detected to be converted into an electric signal. Useful examples of such a device include a combination of a scintillator and a photodiode, and a radioactive ionization chamber.

Figure 9B:
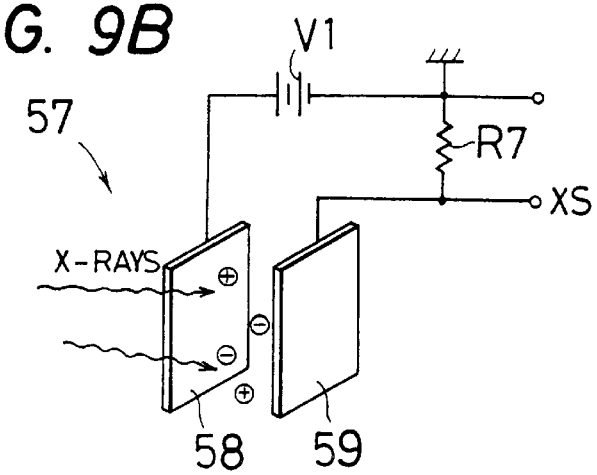
FIG. 9B is a diagram showing an example of a radioactive ionization chamber which is used as an X-ray detecting device 57.

FIG. 9B is a diagram showing an example of a radioactive ionization chamber which is used as the X-ray detecting device 57. A high voltage from a power source V1 is applied to two electrodes 58 and 59 opposite to each other. When X-ray photons enter the space between the electrodes and a part of a filling gas such as air is ionized, positive ions and negative ions are moved toward the cathode and the anode and reach them, respectively. Then, an ionic current flows and an detection signal XS is outputted through both ends of a resistor R7.

Referring again to FIG. 9A, when the X-ray generator 10 radiates X-rays in the form of pulses corresponding to the cycle of commercial power, also the detection signal XS from the X-ray detecting device 57 has a pulse-like form and is supplied to the comparator Q4. In the comparator Q4, the detection signal is compared with a reference voltage defined by resistors R5 and R6 and its waveform is shaped. The output of the comparator Q4 is supplied to the retriggerable timer Q5 to be converted into a digital signal in the form of continuous pulse signal, and the digital signal is outputted as the exposure signal EXP corresponding to the predetermined exposure period and supplied to the image processor 4 shown in FIG. 4.

In this way, the X-ray generation can be surely known by directly detecting X-rays radiated from the X-ray generator 10. The X-ray generation detector shown in FIG. 9 has an advantage that the above-described configuration can be realized only by disposing the X-ray detecting device 57 in an X-ray generation region without changing the manner of connection in a high voltage circuit of an existing X-ray apparatus. Consequently, linkage of an X-ray generator and an X-ray imaging apparatus using a CCD sensor can be easily realized.

Figure 10:
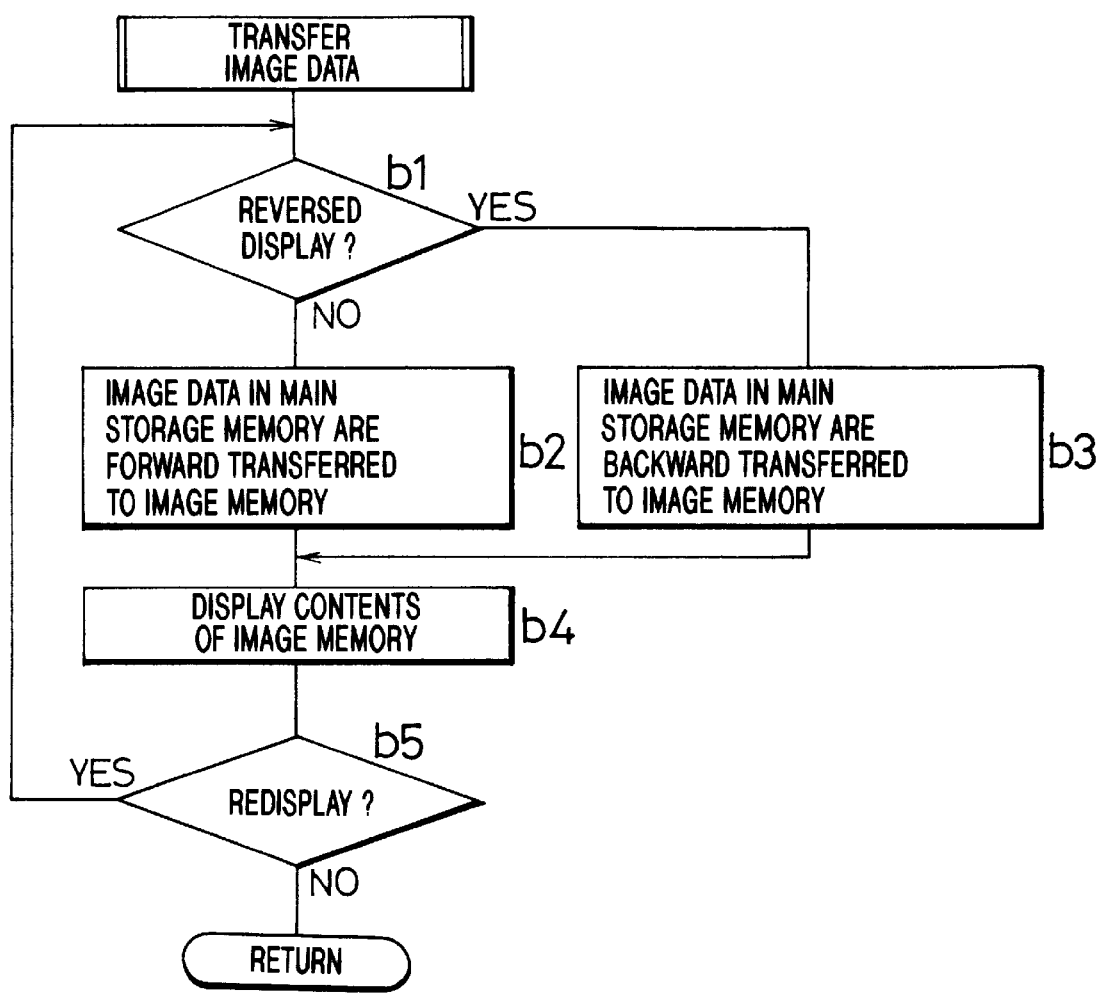
FIG. 10 is a flowchart showing an image data transfer routine in step a10 of FIG. 5.

FIG. 10 is a flowchart showing an image data transfer routine in step a10 of FIG. 5. First, it is judged in step b1 whether the instruction of a reversal display switch 44a of FIG. 4 is a normal display mode or a reversal display mode. If the normal display is instructed, the process proceeds to step b2 in which the CPU 31 conducts the forward transfer to the image memory 34 in accordance with the arrangement of image data in the main storage memory 33. If the reversal display is instructed in step b1, the process proceeds to step b3 in which the CPU 31 conducts the backward transfer to the image memory 34 in such a manner that the arrangement of image data in the main storage memory 33 is mirror-reversed. In step b4, the image data transferred to the image memory 34 are then converted into a video signal VD through the DA converter 35 and then displayed on the monitoring device 5 or the like.

FIGS. 11A, 11B are concept diagrams showing the procedure of transferring data from the main storage memory 33 to the image memory 34. FIG. 11A shows an example of the forward transfer, and FIG. 11B shows an example of the backward transfer. In general, image data consist of a two-dimensional matrix of several hundreds pixels in both the lateral and vertical directions. For the purpose of facilitating the understanding, however, description will be done with using image data having a simplified structure of 4 pixels (lateral)×3 pixels (vertical).

In FIG. 11A, image data consisting of data a11–a34 which are arranged in a two-dimensional matrix are stored in the main storage memory 33. When the CPU 31 conducts the forward transfer, data a11 stored at the pixel which is positioned in the first row and the first column in the main storage memory 33 is transferred to the pixel which is positioned in the first row and the first column in the image memory 34. Then, data a12 stored at the pixel which is positioned in the first row and the second column in the main storage memory 33 is transferred to the pixel which is positioned in the first row and the second column in the video memory 34. In the same manner, data a13 and a14 in the main storage memory 33 are transferred to the pixels which are positioned in the first row and the third column and in the first row and fourth column in the image memory 34, respectively.

The data in the second row are transferred in the same manner. That is, data a21, a22, a23, and a24 in the main storage memory 33 are transferred to the pixels which are positioned in the second row and the first, second, third, and fourth column in the video memory 34, respectively. Similarly, the data of the third row, i.e., data a31, a32, a33, and a34 in the main storage memory 33 are transferred to the pixels which are positioned in the third row and the first, second, third, and fourth column in the image memory 34, respectively.

In this way, the image data in the main storage memory 33 are forward transferred to the image memory 34 in accordance with the arrangement of image data in the main storage memory 33. When the image is displayed according to the arrangement in the image memory 34, an X-ray image as seen from the operator is displayed on the monitoring device 5.

Referring to FIG. 11B, when the CPU 31 conducts the backward transfer, data a11 stored at the pixel which is positioned in the first row and the first column in the main storage memory 33 is transferred to the pixel which is in the first row and the fourth column in the image memory 34. Then, data a12 stored at the pixel which is positioned in the first row and the second column in the main storage memory 33 is transferred to the pixel which is in the first row and the third column in the image memory 34. In the same manner, data a13 and a14 in the main storage memory 33 are transferred to the pixels which are positioned in the first row and the second and first column in the image memory 34, respectively.

The data in the second row are transferred in the same manner. That is, data a21, a22, a23, and a24 in the main storage memory 33 are transferred to the pixels which are positioned in the second row and the fourth, third, second, and first column in the image memory 34, respectively. Similarly, the data of the third row, i.e., data a31, a32, a33, and a34 in the main storage memory 33 are transferred to the pixels which are positioned in the third row and the fourth, third, second, and first column in the image memory 34, respectively.

In this way, the image data in the main storage memory 33 are backward transferred to the image memory 34 so that the arrangement of image data in the main storage memory 33 is mirror-reversed. When the image is displayed according to the arrangement in the image memory 34, an X-ray image as seen from the patient is displayed on the monitoring device 5.

Referring again to FIG. 10, it is judged in step b5 whether the redisplay is instructed through the redisplay switch 44b or not. If the redisplay is instructed, the process proceeds to step b1 and waits for instructions inputted through the reversed display switch 44a. Then, the data transfer and display processes are repeated. If the redisplay is not instructed, the process returns to step a11 of FIG. 5. In next step a11, the CPU 31 resets the busy signal BUSY to be of a low level, and the process returns to step a2 to judge in succession whether the keyboard is operated or not and whether the exposure signal EXP is inputted or not.

Figure 12A:
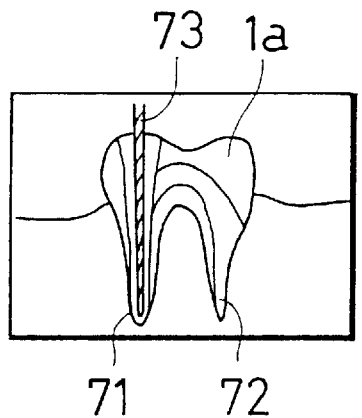
FIG. 12A shows an example of a normal X-ray image display.
Figure 12B:
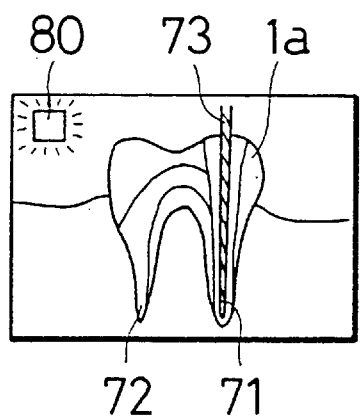
FIG. 12B shows an example of a mirror-reversed X-ray image display.

FIGS. 12A, 12B show examples of an X-ray image display, FIG. 12A shows an example of a normal X-ray display, and FIG. 12B shows an example of a mirror-reversed X-ray display. An X-ray image of the subject 1a such as a tooth is displayed on the monitoring device 5. The image shows that the tip of a reamer 73 reaches the root apex hole of one (root 71) of roots 71 and 72 of the teeth. FIG. 12A corresponds to the X-ray image as seen from the operator, and FIG. 12B corresponds to the X-ray image as seen from the patient. In order to notify an observer that the current display mode is a mirror-reversed display mode, a mode display portion 80 is disposed in which a rectangular region in the upper left corner of the screen blinks to indicate the mirror-reversing. The mode display portion 80 on the screen is formed by a process in which the CPU 31 writes given data stored in the ROM 32 into a region of the image memory 34 which corresponds to the mode display portion 80.

Figure 13A:
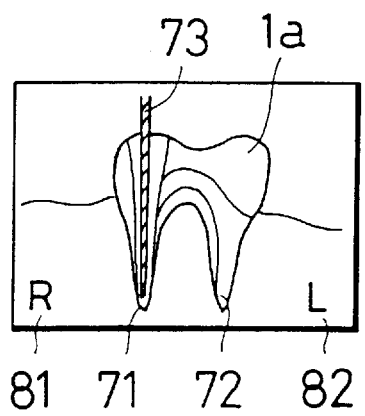
FIG. 13A shows another example of a normal X-ray image display.
Figure 13B:
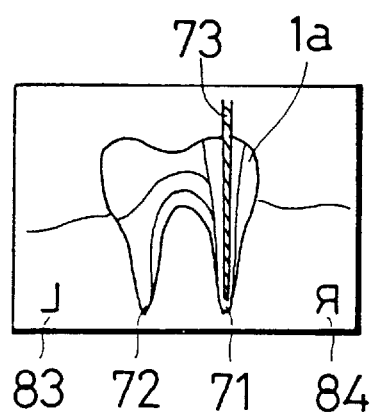
FIG. 13B shows another example of a mirror-reversed X-ray image display.

FIGS. 13A, 13B show other examples of an X-ray image display. FIG. 13A shows an example of a normal display, and FIG. 13B shows an example of a mirror-reversed display. In a similar manner as that of FIG. 12, these figures show the positional relationship between the root apex hole of the root 71 and the tip of the reamer 73. FIG. 13A corresponds to the X-ray image as seen from the operator, and FIG. 13B corresponds to the X-ray image as seen from the patient. These figures are different from FIG. 12 in the following points. In order to notify the observer of the display mode, in FIG. 13A, a character "R" 81 is displayed in the lower left corner of the screen and a character "L" 82 in the lower right corner of the screen, thereby indicating the normal display mode. In FIG. 13B, a mirror-reversed character 83 of "L" is displayed in the lower left corner of the screen and a mirror-reversed character 84 of "R" in the lower right corner of the screen, thereby indicating the mirror-reversed display mode. The characters 81 and 82, and the mirror-reversed characters 83 and 84 on the screens are formed by a process in which the CPU 31 writes given character pattern data stored in the ROM 32 into given regions of the image memory 34.

Figure 14:
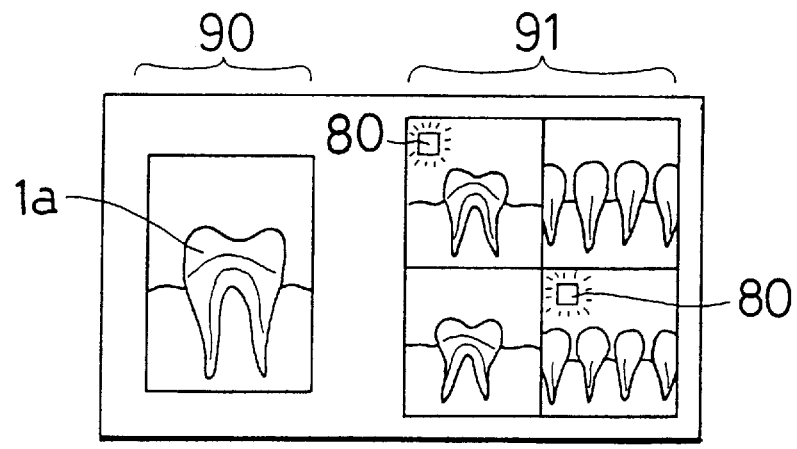
FIG. 14 shows a further example of an X-ray image display.

FIG. 14 shows a further example of an X-ray image display. In the example, a so-called multidisplay having a main screen region 90 and four split screen regions 91 is conducted. An X-ray image which is obtained in the immediately previous X-ray exposure is displayed in the main screen region 90, and X-ray exposure which were obtained in just prior X-ray imaging are displayed in the split screen regions 91. In upper left corners of screens on which a mirror-reversed image is displayed, the mode display portion 80 is formed in which a rectangular region blinks as shown in FIG. 12.

Figure 15:
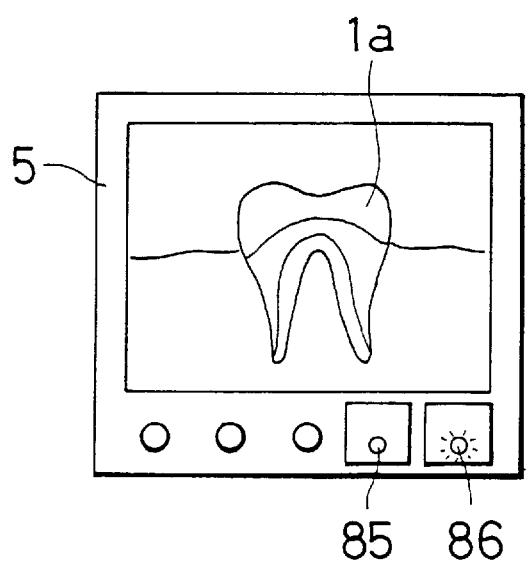
FIG. 15 shows a still further example of an X-ray image display.

FIG. 15 shows a still further example of an X-ray image display. An X-ray image of the subject 1a is displayed on the screen of the monitoring device 5. Of a normal display lamp 85 and a mirror-reversed display lamp 86 which are disposed on an operation panel of the monitoring device 5, the mirror-reversed display lamp 86 blinks to attract the attention of the observer.

FIGS. 12 to 15 show examples in which X-ray images are displayed on the monitoring device 5. When the video printer 6 of FIG. 4 is used, images similar to those described above can be displayed on a recording sheet.

In this way, the fact that the CPU 31 conducts the data transfer while mirror-reversing the data is indicated on the screen of the monitoring device 5, or on a recording sheet output from the video printer 6, by means of the lamps 85 and 86 of the operation panel, whereby enabling the observer to be surely notified of the display mode.

Figure 16:
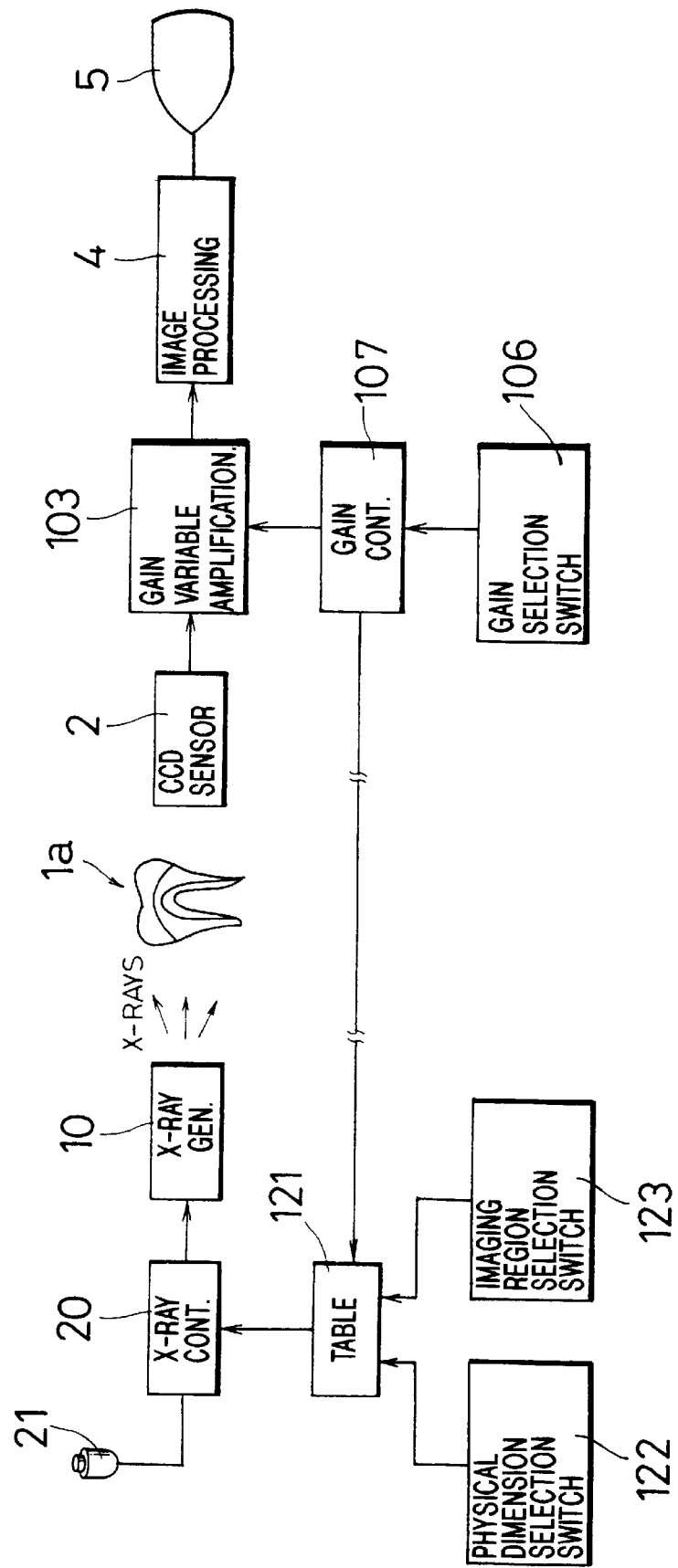
FIG. 16 is a block diagram showing an electrical configuration of a further embodiment of the invention.

FIG. 16 is a block diagram showing an electrical configuration of a further embodiment of the invention. The X-ray imaging apparatus comprises the X-ray generator 10 for irradiating X-rays to the subject 1a such as a tooth; the X-ray controller 20 for controlling the X-ray irradiation period and the like of the X-ray generator 10; the exposure switch 21 for activating the X-ray controller 20 to conduct an X-ray exposure; the imager device 2 for imaging X-rays which have passed through the subject 1a; a gain variable amplifier 103 for amplifying an image signal converted in the imager device 2 with a predetermined gain; the image processor 4 for receiving the image signal outputted from the gain variable amplifier 103 and conducting a predetermined image processing; and the monitoring device 5 and/or a video printer (not shown) for displaying or recording image data processed by the image processor 4. The X-ray imaging apparatus further comprises a gain control unit 107 for controlling the gain of the gain variable amplifier 103; a gain selection switch 106 for indicating a gain to be set to the gain control unit 107; a physical dimension selection switch 122 for inputting information of physical dimensions of a patient 1; an imaging region selection switch 123 for inputting information of an imaging region of the patient 1; and a table 121 for determining the X-ray irradiation period of the X-ray generator 10 on the basis of information of the physical dimensions inputted through the physical dimension selection switch 122, information of the imaging region inputted through the imaging region selection switch 123, and information of the gain selected through the gain selection switch 106.

The X-ray generator 10 operates under a given tube voltage and current. When a high voltage is applied to the X-ray tube in response to the exposure signal outputted from the X-ray controller 20, the X-ray generator 10 generates X-rays. The X-ray dose is adjusted by increasing or decreasing the exposure period. When the tube voltage and current are once set, it is general that they are not frequently changed.

When the exposure switch 21 is pressed down, the X-ray controller 20 outputs to the X-ray generator 10 an exposure signal corresponding to the X-ray generation period, on the basis of the exposure period indicated by the table 121.

In the imager device 2, charges accumulated for a predetermined period are periodically read out on the basis of a given clock signal, whereby excess charges due to thermal excitation and scattered X-rays are prevented from remaining in the device. When the X-ray imaging is to be conducted, the reading operation is stopped and charges are accumulated. After the X-ray imaging, the reading operation is restarted.

The amplification factor of the gain variable amplifier 103 is changed on the basis of a gain signal outputted from the gain control unit 107. Those which are employed as the gain variable amplifier 103 are, for example, an amplifier in which the ratio of feedback resistances of an operational amplifier is changed stepwise by a relay, or a VCA (voltage controlled amplifier) in which the gain can be continuously adjusted by a voltage signal.

As shown in FIG. 17B, for example, the gain selection switch 106 consists of panel switches 106a, 106b, and 106c through which a desired gain can be selected from among the following three modes: a high gain H at which the X-ray dose is reduced and the signal of the imager device 2 is amplified with a high sensitivity; a medium gain M at which the signal is amplified with a medium sensitivity; and a low gain L at which the X-ray dose is increased and the signal is amplified with a low sensitivity. A desired gain is selected by pressing one of the panel switches, and a lamp P disposed above the pressed panel switch lights up. The selectable gains are not restricted to those of the abovementioned three modes. The gain may be adjusted continuously by using a variable resistor or the like.

The gain control unit 107 is configured by the CPU (central processing unit), etc. On the basis of the gain selected through the gain selection switch 106, the gain control unit 107 outputs the gain information to the table 121 as well as the gain signal to the gain variable amplifier 103.

As shown in FIG. 17A, for example, the physical dimension selection switch 122 consists of panel switches 122a, 122b, 122c, 122d through which one of four modes, i.e., child, female, standard, and pyknic can be selected. The physical dimension information of the patient 1 is inputted by pressing one of the panel switches, and a lamp P disposed above the pressed panel switch lights up. The selectable physical dimension information are not restricted to the above-mentioned four modes. The physical dimension information may be adjusted continuously by using a variable resistor or the like.

As shown in FIG. 17A, for example, the imaging region selection switch 123 consists of panel switches 123a to 123g through which a desired imaging region can be selected from among the following seven modes: first to third portions of the upper jaw; first to third portions of the lower jaw;

fourth and fifth portions of the upper jaw; fourth and fifth portions of the lower jaw; sixth to eighth portions of the upper jaw; sixth to eighth portions of the lower jaw; and articulation. The imaging region information of the patient 1 is inputted by pressing one of the panel switches, and a lamp P disposed above or below the pressed panel switch lights up. The selectable imaging region information is not restricted to the above-mentioned seven modes.

The table 121 contains X-ray exposure periods, for example, corresponding in total to 84 (=4×7×3) combinations of the four modes of the physical dimension information, the seven modes of the imaging region information, and the three modes of the gain information, as described above. These X-ray exposure periods are previously stored in a storage device such as a memory. The table 121 indicates to the X-ray controller 20 the X-ray exposure period which is determined in accordance with the inputted information. The thus determined exposure period is displayed on a digit display panel 124 shown in FIG. 17. In place of the table 121, a numeric operation circuit which digitizes information and conducts a predetermined calculation on the digitized information may be used.

Next, the operation will be described. First, the operator observes the physical dimensions of the patient 1 and presses the physical dimension selection switch 122 corresponding to the physical dimensions, and presses the imaging region selection switch 123 corresponding to the imaging region. Then, the operator presses the gain selection switch 106 in accordance with the disease condition to be diagnosed. When a decayed tooth treatment or a root canal treatment is to be conducted, for example, the high gain at which a low X-ray exposure dose and a low image quality are attained is selected, and when periodontitis or cancer is to be treated, the low gain at which a high X-ray exposure dose and a high image quality are attained is selected. In response to the pressing operations, a predetermined exposure period is decided from the combinations which are previously stored in the table 121, and the exposure period is indicated to the X-ray controller 20.

Then, the operator presses the exposure switch 21, and the X-ray controller 20 outputs to the X-ray generator 10 an exposure signal corresponding to the X-ray generation period on the basis of the exposure period indicated by the table 121. The X-ray generator 10 generates X-rays for the exposure period.

When the X-rays pass through the subject 1a and reach the imager device 2, charges corresponding to the X-ray image impinged on the imager device 2 are accumulated, and then outputted as the image signal after the X-ray exposure has been ended. The image signal from the imager device 2 is amplified by the gain variable amplifier 103 with the gain indicated by the gain control unit 107, and then supplied to the image processor 4 in the next stage to be subjected to predetermined image processing. The resulting X-ray image is displayed by the monitoring device 5 or the video printer for the purpose of the use in diagnosis.

As described above, adequate X-ray generation conditions and image processing conditions can be set easily and surely by indicating the physical dimension information, the imaging region information, and the gain information. Moreover, it is possible to obtain an X-ray image which corresponds to the disease condition and is very adequate for diagnosis.

Figure 18:
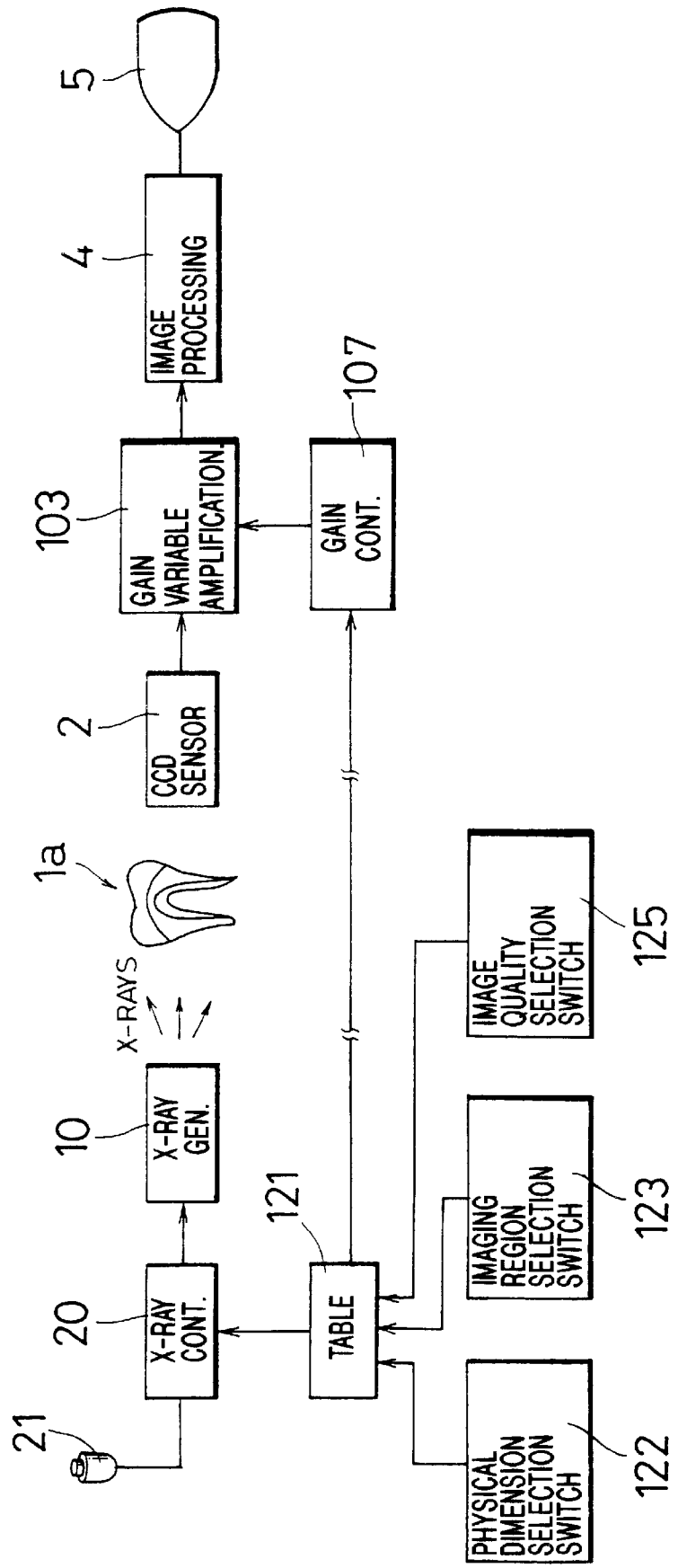
FIG. 18 is a block diagram showing an electrical configuration of a still further embodiment of the invention.

FIG. 18 is a block diagram showing an electrical configuration of a still further embodiment of the invention. The X-ray imaging apparatus of the embodiment is configured in the similar manner as that of FIG. 16, except that the gain selection switch 106 of FIG. 16 is not provided, an image quality selection switch 125 is connected to the table 121, and a gain signal is transmitted from the table 121 to the gain control unit 107.

Figure 19:
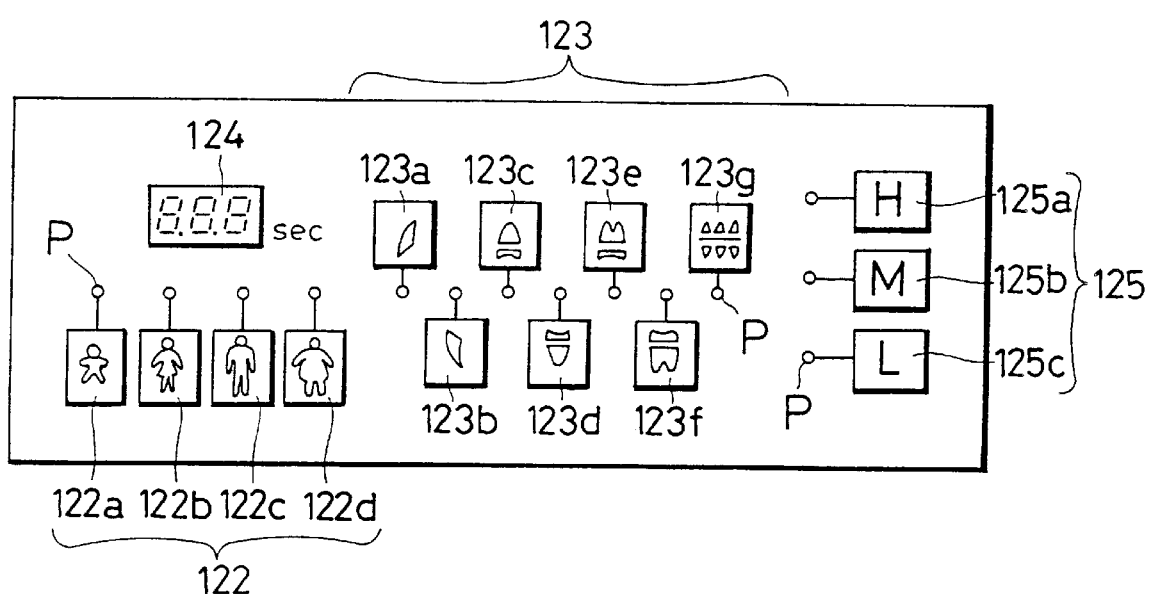
FIG. 19 is a front view showing an example of a physical dimension selection switch 122, an imaging region selection switch 123, and an image quality selection switch 125 of FIG. 18.

As shown in FIG. 19, for example, the image quality selection switch 125 consists of panel switches 125a, 125b, 125c through which a desired image quality can be selected from the following three modes: a high image quality H at which the X-ray exposure dose is increased and a high resolution image is obtained; a medium image quality M at which a standard image quality is obtained; and a low image quality L at which the X-ray exposure dose is reduced and a low resolution image is obtained. A desired image quality is selected by pressing one of the panel switches, and a lamp P disposed in the left side of the pressed panel switch lights up. The selectable image qualities are not restricted to the above-mentioned three modes. The image qualities may be adjusted continuously by using a variable resistor or the like.

In the same manner as that of FIG. 17A, the physical dimension selection switch 122 consists of, for example, as shown in FIG. 19, panel switches 122a, 122b, 122c, 122d through which one of four modes, child, female, standard, and pyknic can be selected.

In the same manner as that of FIG. 17A, the imaging region selection switch 123 consists of, for example, as shown in FIG. 19, panel switches 123a to 123g through which a desired imaging region can be selected from the following seven modes: first to third portions of the upper jaw; first to third portions of the lower jaw; fourth and fifth portions of the upper jaw; fourth and fifth portions of the lower jaw; sixth to eighth portions of the upper jaw; sixth to eighth portions of the lower jaw; and articulation.

The table 121 contains X-ray exposure periods which, for example, correspond in total to 84 (=4×7×3) combinations of the four modes of the physical dimension information, the seven modes of the imaging region information, and the three modes of the image quality information as described above. These X-ray exposure periods are previously stored in a storage device such as a memory. The table 121 indicates to the X-ray controller 20 the X-ray exposure period which is decided in accordance with the inputted information, and indicates to the gain control unit 107 the gain which is determined in accordance with the inputted information. The thus determined exposure period is displayed on a digit display panel 124 shown in FIG. 19. In place of the table 121, a numeric operation circuit in which information digitization and a predetermined calculation on the digitized information are carried out may be used.

The gain control unit 107 is configured by the CPU (central processing unit), etc. On the basis of the gain signal transmitted from the table 121,. the gain control unit 107 outputs the gain signal to the gain variable amplifier 103.

Next, the operation will be described. First, the operator observes the physical dimensions of the patient 1 and presses the physical dimension selection switch 122 corresponding to the physical dimensions, and presses the imaging region selection switch 123 corresponding to the imaging region. Then, the operator presses the image quality selection switch 125 in accordance with the disease condition to be diagnosed. When a decayed tooth treatment or a root canal treatment is to be conducted, for example, the low image quality L is selected, and when periodontitis or cancer is to be treated, the high image quality H is selected. In response to the pressing operations, a predetermined exposure period and a predetermined gain are determined from among the combinations which are previously stored in the table 121, and the determined period and gain are indicated to the X-ray controller 20 and the gain control unit 107, respectively.

Then, the operator presses the exposure switch 21, and the X-ray controller 20 outputs to the X-ray generator 10 an exposure signal corresponding to the X-ray generation period on the basis of the exposure period indicated by the table 121. The X-ray generator 10 generates X-rays for the exposure period.

When the X-rays pass through the subject 1a and reach the imager device 2, charges corresponding to the X-ray image impinged on the imager device 2 are accumulated, and then outputted as the image signal after the X-ray exposure has been ended. The image signal from the imager device 2 is amplified by the gain variable amplifier 103 with the gain indicated by the gain control unit 107, and then supplied to the image processor 4 in the next stage to be subjected to predetermined image processing. The resulting X-ray image is displayed by the monitoring device 5 or the video printer for the purpose of the use in diagnosis.

As described above, adequate X-ray generation conditions and image process conditions can be set easily and surely by indicating the physical dimension information, the imaging region information, and the image quality information. Moreover, it is possible to obtain an X-ray image which corresponds to the disease condition and is very adequate for diagnosis.

In the above, examples in which a CCD sensor is used as the imager device 2 have been described. Alternatively, another imager device such as an X-ray television camera, and an image intensifier may be also used.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. An X-ray imaging apparatus for irradiating X-rays generated by an X-ray generator, to a subject to take an X-ray image of the subject, the X-ray imaging apparatus comprising:

an image device capable of being inserted into an oral cavity, for detecting the X-ray image of the subject and converting the X-ray image into electrical signals;

an image processor for reading the X-ray image detected by the imager device into a memory and conducting a predetermined image processing to display the X-ray image on a monitor; and electric current detection means for being mounted on the X-ray generator, for detecting an electric current supplied to a high voltage circuit composing the X-ray generator, wherein reading of the X-ray image from the imager device is started on the basis of an exposure signal from the electric current detection means.

2. An X-ray imaging apparatus for irradiating X-rays generated by an X-ray generator, to a subject to take an X-ray image of the subject, the X-ray imaging apparatus comprising:

an imager device, capable of being inserted into an oral cavity, for detecting the X-ray image of the subject and converting the X-ray image into electrical signals;

an image processor for reading the X-ray image detected by the imager device into a memory and conducting a predetermined image processing to display the X-ray image on a monitor, and electric power detection means for being mounted on the X-ray generator, for detecting an electric power supplied to a high voltage circuit composing the X-ray generator, wherein reading of the X-ray image from the imager device is started on the basis of an exposure signal from the electric power detection means.

* * * * *